US012605458B2

(12) United States Patent
Zhu et al.

(10) Patent No.: US 12,605,458 B2
(45) Date of Patent: Apr. 21, 2026

(54) ANTIBODY-DRUG CONJUGATE HAVING ACIDIC SELF-STABILIZATION JUNCTION

(71) Applicant: SICHUAN BAILI PHARMACEUTICAL CO. LTD., Chengdu (CN)

(72) Inventors: Yi Zhu, Chengdu (CN); Yiqian Wang, Chengdu (CN); Jie Li, Chengdu (CN); Shi Zhuo, Chengdu (CN); Weili Wan, Chengdu (CN)

(73) Assignee: SYSTIMMUNE, INC., Redmond, WA (US)

( * ) Notice: Subject to any disclaimer, the term of this patent is extended or adjusted under 35 U.S.C. 154(b) by 1502 days.

(21) Appl. No.: 16/971,219

(22) PCT Filed: Jun. 15, 2018

(86) PCT No.: PCT/CN2018/091621

§ 371 (c)(1),
(2) Date: Aug. 19, 2020

(87) PCT Pub. No.: WO2018/233571

PCT Pub. Date: Dec. 27, 2018

(65) Prior Publication Data

US 2021/0100912 A1 Apr. 8, 2021

(30) Foreign Application Priority Data

Jun. 19, 2017 (CN) ........................ 201710462790.9

(51) Int. Cl.

| | |
|---|---|
| ***A61K 47/68*** | (2017.01) |
| ***A61K 45/06*** | (2006.01) |
| ***A61K 47/54*** | (2017.01) |
| ***A61K 47/65*** | (2017.01) |
| ***A61P 35/00*** | (2006.01) |

(52) U.S. Cl.

CPC ........ *A61K 47/6889* (2017.08); *A61K 47/545* (2017.08); *A61K 47/65* (2017.08); *A61K 47/68031* (2023.08); *A61K 47/6849* (2017.08); *A61K 47/6851* (2017.08); *A61K 45/06* (2013.01); *A61P 35/00* (2018.01)

(58) Field of Classification Search

CPC .. A61K 47/6889; A61K 47/545; A61K 47/65; A61K 47/68031; A61K 47/6849; A61K 47/6851; A61K 45/06; A61K 47/6859; A61K 38/07; A61K 47/6803; A61P 35/00; A61P 29/00; A61P 37/02; C07K 16/303

See application file for complete search history.

(56) References Cited

U.S. PATENT DOCUMENTS 9,504,756 B2 11/2016 Lyon et al.

FOREIGN PATENT DOCUMENTS

| | | | |
|---|---|---|---|
| CN | 103648532 | A | 3/2014 |
| CN | 104758946 | A | 7/2015 |
| CN | 106029083 | Y | 10/2016 |
| WO | WO2004010957 | A | 2/2004 |
| WO | WO2016147031 | Y | 9/2016 |

OTHER PUBLICATIONS

Tiberghien, et al, ACS Med. Chem. Lett. 2016 7:983 (Year: 2016).*
Fontaine, et al., Bioconjugate Chem 2015 26:145 (Year: 2015).*
DeRuiter, et al. Principles of Drug Action I 2005 available online at: https://webhome.auburn.edu/~deruija/pda1_resonance.pdf; accessed Mar. 27, 2024 (Year: 2005).*
Sigma-Aldrich, Glycine methyl ester HCL product, 1999, URL: https://www.sigmaaldrich.com/US/en/product/aldrich/g6600; Accessed Mar. 27, 2024 (Year: 1999).*
Organic Chemistry Portal, Protecting Groups (methyl esters), 2005, URL: https://www.organic-chemistry.org/protectivegroups/carboxyl/methyl-esters.htm; Accessed Mar. 27, 2024 (Year: 2005).*
Organic-Chemistry.com (URL=https://www.organic-chemistry.org/protectivegroups/carboxyl/benzyl-esters.htm; Accessed Jan. 10, 2025) (Year: 2025).*
Ashenhurst, J, "How to Use a pKa Table"; URL: https://www.masterorganicchemistry.com/2010/06/18/know-your-pkas/; Published Jun. 18, 2010; Accessed Jan. 24, 2025 (Year: 2010).*

* cited by examiner

*Primary Examiner* — Julie Wu
*Assistant Examiner* — Sydney Van Druff
(74) *Attorney, Agent, or Firm* — EpiMED LLC

(57) ABSTRACT

The present invention provides a special drug conjugate having a hydrophilic acidic stabilization junction. Compared with a conjugate having a lower drug loading, due to the introduction of the acidic stabilization junction, the conjugate in the present invention can also have a higher drug loading (that is, each targeted reagent has more hydrophilic drug junctions), keeps a desired PK property and has a same or better activity in a body.

18 Claims, 6 Drawing Sheets

ANTIBODY-DRUG CONJUGATE HAVING ACIDIC SELF-STABILIZATION JUNCTION

TECHNICAL FIELD

The present invention relates to the application of an antibody-drug conjugate for the treatment of cancer or other diseases, and in particular to the application of a special hydrophilic acidic stabilization junction in the preparation of antibody-drug conjugate to increase drug stability in plasma while at the same time significantly improving pharmacokinetics (PK).

BACKGROUND ART

Antibody-drug conjugates (ADCs) are a class of novel targeted drugs which generally consist of three components: an antibody or antibody-like ligand, a small-molecule drug, and a linker that couples the antibody to the drug. Antibody-drug conjugates make use of the specific recognition of certain antigens by antibodies to transport drug molecules to the vicinity of target cells and release them effectively in order to provide a therapeutic effect. In August 2011, the U.S. Food and Drug Administration (FDA) approved Seattle Genetics' new ADC, Adecteis™, for the treatment of Hodgkin's lymphoma as well as anaplastic large cell lymphoma (ALCL), and clinical application has demonstrated the safety and efficacy of this class of drugs.

For antibody-drug conjugates, in order to ensure the efficient attachment of the drug molecule to the antibody, conjugates currently entering clinical trials are typically attached via linkers to lysine residues on the surface of the ligand or to cysteine residues (obtained by partial reduction of interchain disulfide bonds) in the hinge region of the antibody. However, the presence of a large number of lysine residues (more than 80) on the antibody surface and the non-selective nature of the coupling lead to uncertainty in the number of couplings and sites, which in turn leads to a lack of homogeneity in antibody-drug conjugates. Sulfhydryl coupling can effectively mitigate the problem of poor product quality consistency, and maleimide serving as a linker can rapidly and highly selectively form thioether products with antibody sulfhydryl groups under mild conditions.

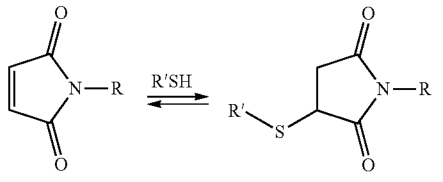

Thioether

However, an increasing number of studies have shown that the addition of succinimide with sulfhydryl is a reversible process (inverse Michael addition), and when the addition product enters the plasma, exchange of the addition product with an albumin sulfhydryl group, resulting in shedding of the drug molecule, can be clearly observed via the presence of a large number of proteins containing free sulfhydryl groups in the plasma. The shedding of the drug molecule on the one hand produces toxic side effects while on the other hand reducing the efficacy of the antibody-drug conjugate. (See Shen, et al. "Conjugation site modulate the vivo stability and therapeutic activity of antibody-drug conjugates" Nature Biotech (2012) 30:184-189; Baldwin & Kiick, Bioconj. Chem 2011, 22, 1946-1953; Alley, et al. Bioconjugate Chem. 2008, 19, 759-765.)

Many investigators have carried out published studies with the goal of improving the stability of antibody-drug conjugates in plasma and reducing sulfhydryl group reverse Michael addition. It has been reported that the cyclic thioether addition product formed by maleimide and sulfhydryl can undergo hydrolysis in an aqueous environment to form a thioether ring-opened product. Unlike cyclic sulfide addition products, sulfide ring-opened products remain stable in plasma and are no longer exchanged with other sulfhydryl groups. Therefore, the exchange of sulfhydryl groups can be effectively avoided if all of an antibody-drug conjugate is converted to a ring-opened structure before it enters the body.

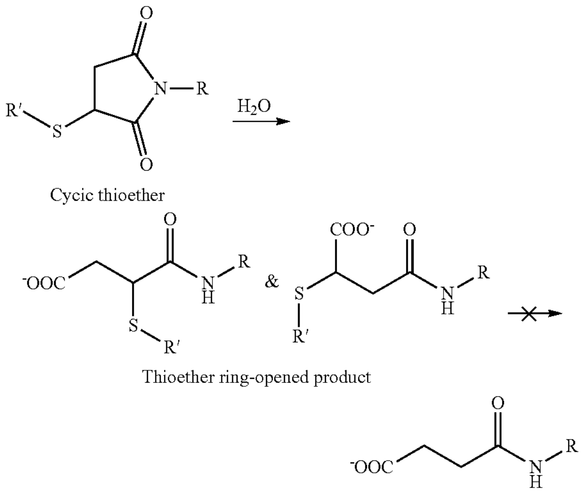

Cycic thioether

&

Thioether ring-opened product

The speed of an additive ring-opening reaction is influenced by many factors including the pH and temperature of the reaction as well as the structure subject to the reaction and due to the sensitivity of antibodies to pH and temperature, rapid ring-opening at a pH and temperature that the antibody can tolerate is best achieved by optimizing the link structure. Patent WO2016025752 discloses a method whereby a strong electron-attracting group is introduced outside the succinimide ring, wherein said method leverages electron-absorbance to reduce the exchange of thioether addition products with albumin; however, it is precisely because of the presence of said electron-absorbing group that the succinimide and drug linkage is difficult to preserve under natural conditions and succinimide bearing a strong electron-attracting group is highly susceptible to ring hydrolysis after which it is no longer able to undergo further addition with thioether.

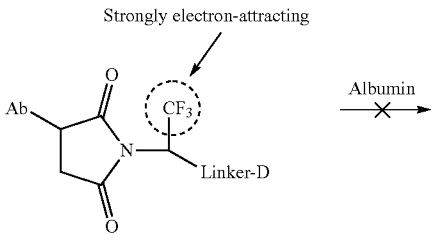

-continued

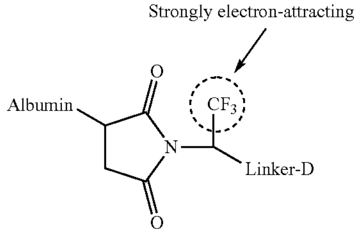

Seattle Genetics (US) Patent No. US20130309256 discloses a linker that introduces a basic group and an electron-attracting group next to the succinimide, wherein the albumin exchange rate of the addition product can be effectively reduced due to the effect of the basic group, significantly improving stability in plasma. As is generally known, the pH of human plasma is weakly basic and although the incorporation of basic groups can promote the succinimide ring-opening, improving the hydrophilicity of the entire molecule becomes more difficult. This phenomenon is well confirmed in a subsequent Seattle Genetics patent, WO2015057699. After incorporating a stabilization junction bearing a basic group into a target molecule, the inventors of the present invention discovered the entire antibody-drug conjugate molecule was still rapidly degraded in mice at higher drug loads due to hydrophobicity (see Patent No. WO2015057699, Page 225), and to improve the above situation, the inventors were forced to introduce a complex polyethylene glycol structure into the side chain of the molecule to improve the aggregation of the molecule (see Patent No. WO2015057699).

In addition to reducing albumin exchange and improving plasma stability, another important factor that must be considered in antibody-drug conjugate design is the amount of drug that can be delivered per targeting agent (i.e., the quantity of cytotoxic agent attached to each targeting agent (e.g., each antibody)), which is referred to as the drug load. It has been hypothesized that higher drug loads produce better efficacy than lower drug loads (e.g., an 8-unit load should exhibit better in vivo and in vitro efficacy compared to a 4-unit load). The rationale for this theory is that conjugates with higher drug loads will deliver more drug (cytotoxic agent) to target cells. Results obtained in vitro have also confirmed that conjugates with higher drug loads exhibit higher activity against cell lines in vitro. However, certain subsequent studies have revealed that this hypothesis has yet to be similarly confirmed in vivo in animal models. It has been observed in the literature that conjugates with 4-unit and 8-unit drug loads of an auristatin have unexpectedly similar activity in a murine model, and no higher efficacy was observed under an 8-unit drug load. See Hamblett, et al., Clinical Cancer Res. 10:7063-70 (2004). Hamblett et al. revealed the reasons for the above experimental phenomenon and further reported that higher load ADCs are cleared from circulation more quickly in animal models. This faster clearance indicates a tendency for higher load conjugates to have more unstable PKs compared to lower load conjugates. In addition, higher load conjugates exhibit a lower MTD in mice and thus have a narrower therapeutic index. In contrast, ADCs with a load of two at an artificially modified site on a monoclonal antibody were reported to have the same or better PK properties and therapeutic indices than some four-unit load ADCs. See reports published by Junutula, et al., Clinical Cancer Res. 16:4769 (2010).

Increasing the drug load theoretically increases the amount of drug carried by a single antibody into the target cell, however, due to the hydrophobicity of the drug, the hydrophobicity of an ADC will increase as drug quantity is increased, resulting in ADC aggregation in the body and a reduced therapeutic index. Alternative methods to overcome the tendency for higher load ADCs to exhibit less desirable PK properties include the addition of solubilizing groups to the ADC structure. For example, a polyethylene glycol polymer or other water-soluble polymer can be added to the linker (e.g., the area between the drug and antibody bonding sites) in order to overcome the tendency for the ADC to aggregate. For example, despite the fact that Seattle Genetics has developed the ability to stabilize junctions via the incorporation of basic groups, there is still a need to improve the PK of drug molecules at high loads, by, for example, introducing side chain PEGs into the junction-drug conjugate. However, the addition of solubilizing groups increases the complexity of the preparation process used for such conjugates.

Therefore, a new approach is urgently needed in the field of novel ADCs used to ameliorate the detrimental effects of high drug to antibody ratio (DAR) that can simultaneously overcome the increase in plasma stability caused by succinimide sulfhydryl exchange while also improving the pharmacokinetic properties of antibody-drug conjugates with a high DAR. The acidic stabilization junction constituted by the present invention remarkably meets both of the above requirements.

SUMMARY OF THE INVENTION

The present invention seeks to provide a special hydrophilic acidic stabilization junction-drug conjugate. While conducting experiments, the inventors of the present invention were surprised to find that, unlike the introduction of basic groups described in US20130309256, the introduction of an acidic amino acid or oligopeptide unit reduces succinimide and antibody conjugate sulfhydryl exchange while maintaining a high degree of stability in blood plasma. It was also experimentally demonstrated that the designed conjugate exhibits a similar level of hydrophilicity to unconjugated targeting reagent due to the incorporation of one or more amino acids, thus retaining pharmacokinetic (PK) properties similar to those of the unconjugated targeting reagent in vivo. Therefore, the presence of an acidic stabilization junction contributes to the efficacy of the drug through the above two pathways that together increase the stability of the drug in plasma and improve the drug's pharmacokinetics (PK).

The introduction of an acidic stabilization junction also allows the conjugate to have a higher drug load (i.e., a higher quantity of hydrophilic drug junctions per targeting reagent) compared conjugates with a lower drug load, while retaining desired PK properties and exhibiting the same or better activity in vivo. (For example, a 4-unit load or 8-unit load conjugate may have the same or better PK properties than their 2- or 4-unit load counterparts, respectively; such 4-unit load or 8-unit load conjugates may have the same or better PK properties than their 2- or 4-unit load counterparts, respectively.)

Specifically, the present invention provides an antibody-drug conjugate or a pharmaceutically acceptable salt thereof as shown in Formula I:

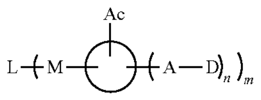

Where:

L corresponds to an antibody, antibody fragment or protein;

M corresponds to succinimide or hydrolyzed succinimide;

Ac corresponds to a fragment consisting of an amino group and acidic group or an oligopeptide consisting of a plurality of amino acids wherein the amino portion is connected to the circle shown;

D corresponds to the drug portion;

A corresponds to the linker portion;

The circle indicates a scaffold, corresponding to a substituted or unsubstituted $C_{1-8}$ alkylidene, $C_{1-8}$ heteroalkylidene, $C_{6-10}$ arylidene or $C_{4-10}$ heteroarylidene.

m corresponds to an integer ranging from 1 to 20, and n corresponds to 1 or 2.

Preferably, said antibody corresponds to an antibody for a cell surface receptor and tumor-associated antigen.

Preferably, Ac corresponds to an acidic amino acid unit or acidic oligopeptide.

More preferably, Ac preferably corresponds to a natural amino acid or unnatural amino acid having an isoelectric point of 7.0 or less or an oligopeptide composed of the same.

In some preferred examples, the oligopeptide unit preferably consists of 2 to 5 amino acids.

In some preferred examples, A corresponds to a cleavable linker or a non-cleavable linker.

In some preferred examples, said drug corresponds to a cytotoxic drug, drug for treating autoimmune disease and anti-inflammatory drug.

More preferably, the drug D is selected from a set comprising maitansine drugs, australin drugs, benzodipyrrole drugs, pyrrolozodiazole drugs, amantin or derivatives thereof and camptothecine compounds.

In some preferred examples, A has the following formula:

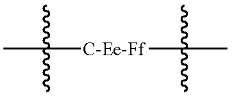

Where C corresponds to an optional extensible unit at the end, E corresponds to an optional breakable unit, F corresponds to a spacer unit and subscripts e and f correspond to 0 or 1. The wavy line indicates a connection site between the acidic self-stabilization junction and a drug unit.

In some preferred examples, the circle represents a $C_{1-8}$ alkylene group or a $C_{1-8}$ heteroalkylene group.

More preferably, the circle represents a $C_{1-3}$ alkylene group;

In some preferred examples, Ac is selected from a set comprising (D/L) glycine, (D/L) alanine, (D/L) leucine, (D/L) isoleucine, (D/L) valine, (D/L) phenylalanine, (D/L) proline, (D/L) tryptophan, (D/L) serine, (D/L) tyrosine, (D/L) cysteine, (D/L) methionine, (D/L) asparagine, (D/L) glutamine, (D/L) threonine, (D/L) aspartic acid, (D/L) glutamic acid, or the following structural formulas:

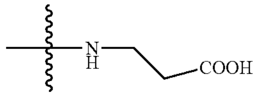

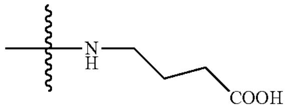

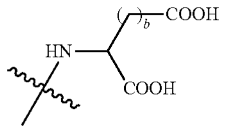

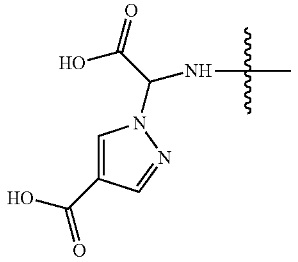

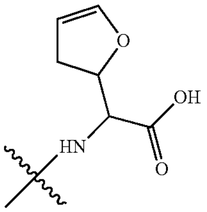

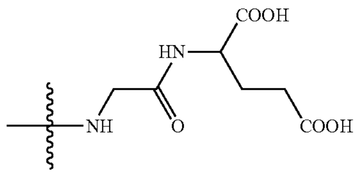

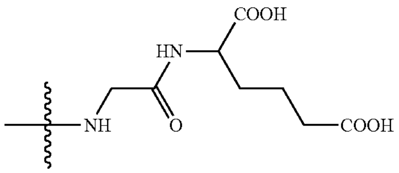

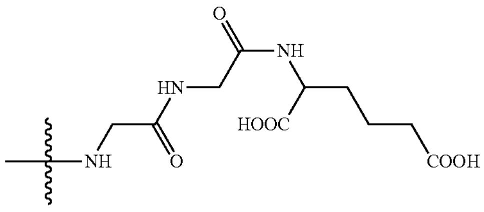

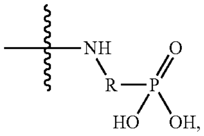

Where a wavy line indicates a linkage site to the scaffold and R corresponds to an arbitrary linkage fragment between an amino group and a phosphate group.

Another aspect of the present invention provides a junction-drug linkage having the following structure:

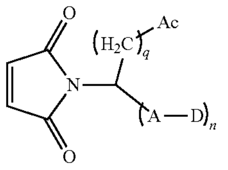

Ac corresponds to an amino acid unit with an isoelectric point less than 7;

D corresponds to the drug portion;

A corresponds to the linker portion;

q corresponds to an integer ranging from 1 to 8, and n corresponds to 1 or 2.

The present invention provides an antibody-drug conjugate or pharmaceutically acceptable salt thereof, as well as a pharmaceutically acceptable diluent carrier or excipient pharmaceutical composition.

The antibody-drug conjugate or pharmaceutically acceptable salt thereof is used in the preparation of drugs for the treatment of cancer, immune disease, and inflammation.

SPECIFIC EMBODIMENTS

Figure 1:
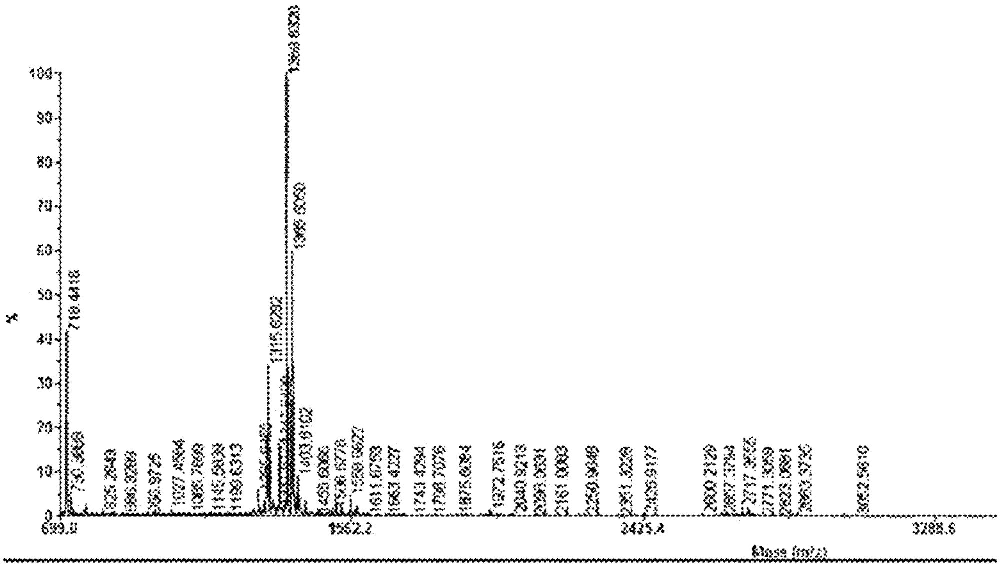
FIG. 1 shows MS-TOF assay results obtained for Compound 11.
Figure 2A:
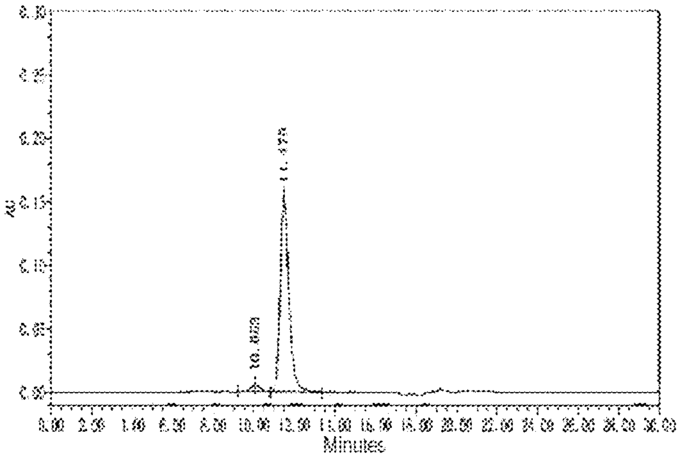
FIG. 2A shows SEC-HPLC assay results obtained for H-11.
Figure 2B:
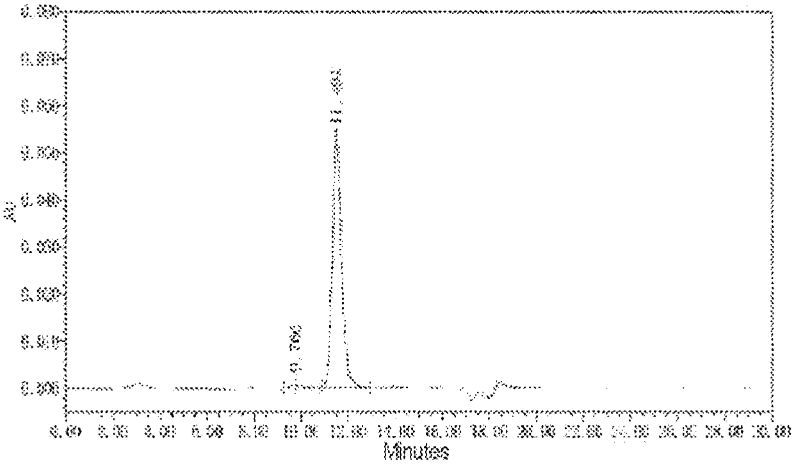
FIG. 2B shows SEC-HPLC assay results obtained for H-20.
Figure 2C:
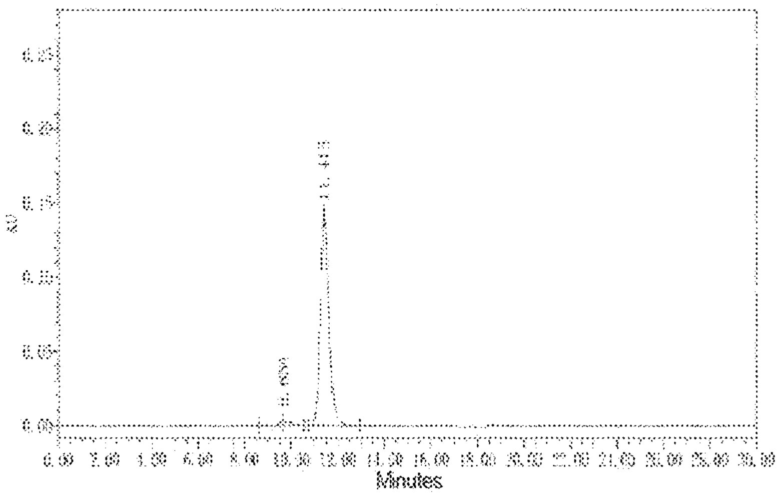
FIG. 2C shows SEC-HPLC assay results obtained for H-29.
Figure 2D:
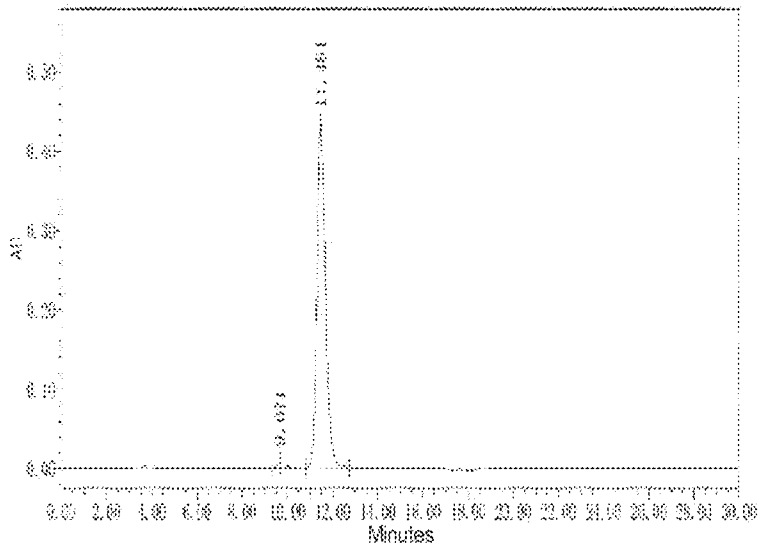
FIG. 2D shows SEC-HPLC assay results obtained for H-39.
Figure 2E:
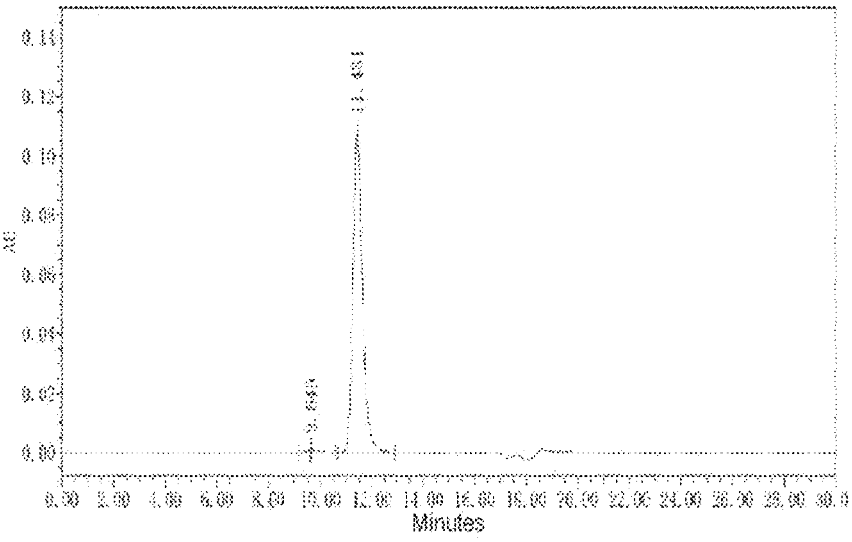
FIG. 2E shows SEC-HPLC assay results obtained for H-41.
Figure 2F:
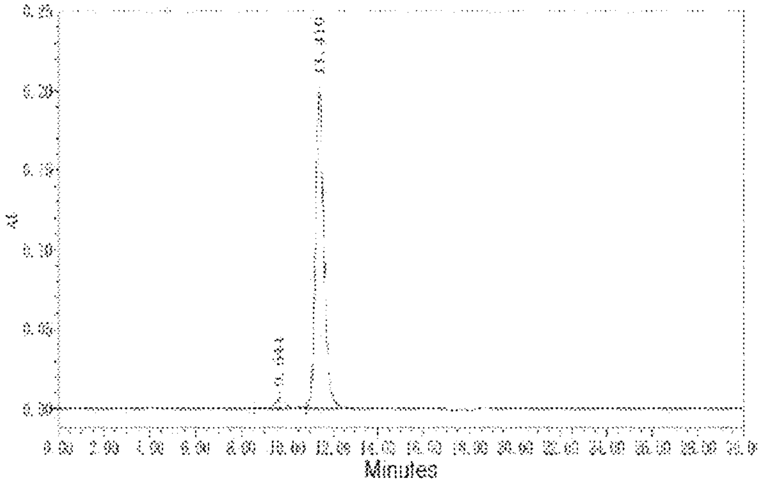
FIG. 2F shows SEC-HPLC assay results obtained for H-43.
Figure 2G:
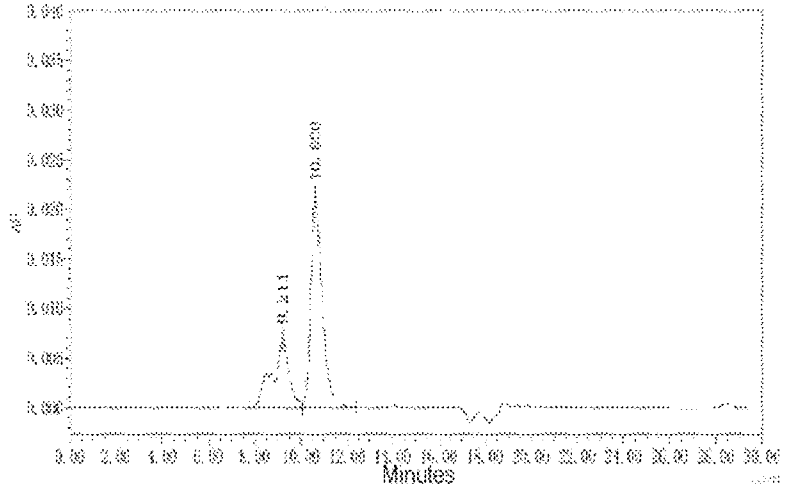
FIG. 2G shows SEC-HPLC assay results obtained for MC-VC-PAB-MMAE.
Figure 2H:
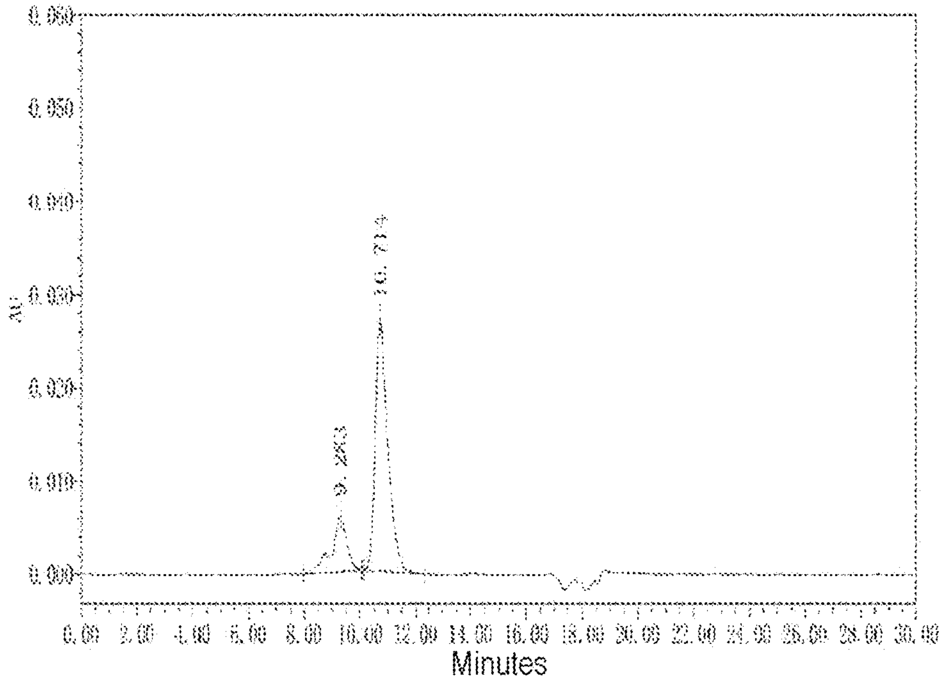
FIG. 2H shows SEC-HPLC assay results obtained for DPR-VC-PAB-MMAE.

Following extensive and intense research efforts, the inventors of the present invention were surprised to find that antibody-drug conjugates having an acidic stabilization junction exhibit better stability in plasma and are more hydrophilic than conventional antibody-drug conjugates, and that the conjugated structures can withstand higher load while maintaining the desired pharmacokinetic properties of the structures at low loadings. A higher drug load leads to better activity and therapeutic efficacy.

Specifically, an antibody-drug conjugate having an acidic stabilization junction provided by the present invention has a maleimide unit which, upon coupling with the antibody sulfhydryl group and with the participation of the stabilizing acidic group, hydrolyzes the ring, and the resulting structure does not undergo exchange with other sulfhydryl-containing macromolecules in plasma, thus preventing shedding of the drug molecule.

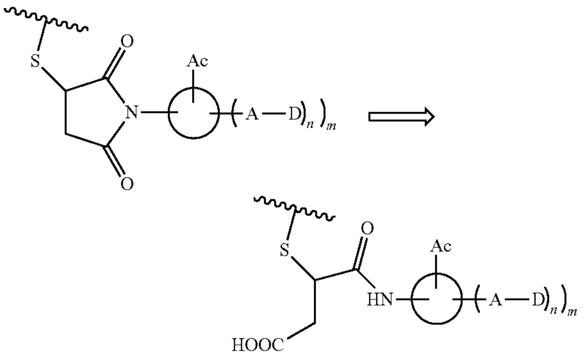

At the same time, the presence of one or more hydrophilic acidic groups results in the formation of a ring-opened structure that is more hydrophilic than the antibody-drug conjugate, thereby preventing problems such as decreased activity due to an increased drug load.

The resulting antibody-drug conjugate may be used to ensure that drug reaches a target cell population, such as a group of tumor cells. The antibody-drug conjugate specifically binds to cell surface proteins, and the resulting bonds are randomly endocytosed. Within the cell, the drug is released in the form of an active drug to produce one or more effects. Antibodies include chimeric antibodies, humanized antibodies, human antibodies; antibody fragments that can bind to antigens; antibody Fc fusion proteins; or proteins. Viable drugs are highly active drugs, including, but not limited to, maytansinoids, auristatins, calicheamicins, doxorubicins, benzodipyrrole antibiotics (duocarmycins and CC-1065), pyrrolobenzodiazepine dimers (PBDS), goitrogens, camptothecin and derivatives such as SN38, irinotecan, and ixitecan.

DETAILED DESCRIPTION OF THE PATENT

Abbreviations and Definitions

Unless otherwise indicated, the following terms and phrases used herein are intended to have the following meanings. When a trademarked name is used herein, unless the context indicates otherwise, the trademarked name shall include the product formulation, generic drug, and active pharmaceutical ingredient of said trademarked product.

The term "alkylene" refers to a bivalent straight chain saturated hydrocarbon group with 1 to 20 carbon atoms, including groups ranging from 1 to 10 carbon atoms. Examples of alkylene groups include, but are not limited to, methylene (—CH2-), ethylene (—CH2-CH2-), n-propylene, n-butylene, n-pentylene, n-hexylene, etc. Unless otherwise indicated, the term "aryl" shall refer to a polyunsaturated, generally aromatic, hydroxyl group, which may be monocyclic or a fused or covalently linked polycyclic ring (with up to three rings). The term "heteroaryl" refers to an aryl group (or ring) containing 1 to 5 heteroatoms selected from a set comprising N, O and S, wherein nitrogen and sulfur atoms may be optionally oxidized, and nitrogen atoms may optionally be subject to quaternary ammoniation. A heteroaryl group can be attached to the rest of the molecule via a heteroatom. Non-limiting examples of aryl groups include: phenyl, naphthyl and diphenyl, while non-limiting examples of heteroaryl groups include: pyridyl, pyridazinyl, pyrazinyl, pyrimidinyl (pyrimindinyl), triazinyl, quinolinyl, quinoxalinyl, quinazolinyl, misolinyl, phthalaziniyl, benzotriazinyl, purinyl, benzimidazolyl, benzopyrazolyl, benzotriazolyl, benzotriazolyl, isobenzofuranyl, isoindolyl, indolyl, benzotriazinyl, thienopyridinyl, thienopyrimidinyl, pyrimidinyl, imidazopyridine, benzothiazolyl, benzofuranyl, benzothienyl, indolyl, quinolinyl, isoquinolinyl, isothiazolyl, pyrazolyl, indolyl, tyridinyl, imidazolyl, triazolyl, tetrazolyl, oxazolyl, isoxazolyl, thiadiazolyl, pyrrolyl, thiazolyl, furanyl, thienyl, etc. When described as "substituted," the substituents of the aromatic and heteroaromatic systems described above are selected from acceptable substituents as given below.

As referred to in the present patent, an arylidene group refers to the presence of two covalent bonding structures in the aforementioned aryl structure in the ortho-, meta- or para-position.

Unless otherwise specified herein, substituents constituted by hydrocarbon groups (including those commonly referred to as alkylidene, alkenyl, alkynyl and cycloalkyl) may correspond to a variety of different groups selected from the following set: -halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)═NH, —NR'C($NH_2$)═NH, —NH—C($NH_2$)═NR', —S(O)R', —S(O)$_2$R', —S(O)$_2$NR'R", —NR'S(O)$_2$R", —CN and —$NO_2$, with the number of substituents ranging from 0 to (2m'+1), where m' is the total number of carbon atoms in the group. R', R" and R" each independently correspond to a hydrogen atom, unsubstituted $C_{1-8}$ alkyl, unsubstituted aryl, aryl substituted with 1 to 3 halogen atoms, unsubstituted $C_{1-8}$ alkyl, $C_{1-8}$ alkoxy or $C_{1-8}$ thioalkoxy, or an unsubstituted aryl-$C_{14}$ alkyl group. When R' and R" are attached to the same nitrogen atom, they can form 3-, 4-, 5-, 6- or 7-element rings with said nitrogen atom. For example, —NR'R" includes 1-pyrrolidinyl and 4-morpholinyl.

As used herein, the "derivative" of a compound refers to a substance that has a chemical structure similar to that of the corresponding compound but which also contains at least one chemical group that is not present in the compound and/or lacks an at least one chemical group that is present in the compound. The compound to which the derivative is compared is referred to as the "parent" compound. Generally, a "derivative" may be produced from the parent compound via one or more chemical reaction steps.

Antibodies, Antibody Fragments and Proteins

In the embodiments of the present invention, antibodies, antibody fragments and protein units correspond to targeting agents that specifically bind to a target element. Antibodies as described in the context of the present invention are capable of binding specifically to cellular components or to other target molecules of interest. In some aspects, the antibody unit acts to deliver the drug unit to a specific target cell population with which the ligand unit interacts. Ligands may include, but are not limited to, proteins, polypeptides and peptides, as well as non-proteins such as sugars. Suitable ligand units include, for example, antibodies, such as full-length (complete) antibodies as well as antigen-binding fragments thereof. In embodiments where the ligand unit is a non-antibody targeting reagent, it may correspond to a peptide or polypeptide, or a non-protein molecule. Examples of such targeted reagents include interferons, lymphokines, hormones, growth and colony-stimulating factors, vitamins, nutrient transport molecules, or any other cell-binding molecule or substance. In some embodiments, the linker is covalently attached to a sulfur atom on the ligand. In some aspects, the sulfur atom is the sulfur atom of the cysteine residue, which forms the interchain disulfide bond of the antibody. In another aspect, the sulfur atom is a cysteine residue that has been introduced into the ligand unit and which forms the antibody's interchain disulfide bond. In another aspect, the sulfur atom is a sulfur atom of a cysteine residue that has been introduced into the ligand unit (e.g., via site-directed mutagenesis or chemical reaction). In other aspects, the linker-bound sulfur atom is selected from a cysteine residue that forms the interchain disulfide bond of the antibody or a frontal cysteine residue that has been introduced into the ligand unit (e.g., via site-directed mutagenesis or chemical reaction). In some embodiments, the EU index numbering system as defined by Kabat (Kabat E. A., et al., (1991) Sequences of proteins of Immunological Interest, Fifth Edition, NIH Publication 91-3242) is used.

As used in this patent, "antibody" or "antibody unit" includes, within the scope thereof, any part of the antibody structure. This unit can bind to, reactively associate with, or form a complex with, a receptor, antigen, or other target receptor unit belonging to the cell population. An antibody can be any protein or protein-like molecule that binds, complexes, or reacts with part of the population of cells targeted for treatment or biological modification.

The antibodies used in the present patent include polyclonal antibodies and monoclonal antibodies wherein said polyclonal antibodies are heterogeneous groups of antibody molecules derived from the serum of an immune animal. Monoclonal antibodies include, but are not limited to, murine and human monoclonal antibodies, humanized monoclonal antibodies or chimeric monoclonal antibodies, and antibodies derived from other species. Human monoclonal antibodies can be produced by any of the many techniques known in the field (e.g., Teng, et al. 1983, proc. Natl. Acad. Sci. USA. 80:7308-7312; Olsson, et al. 1982, MEthan, Enzymol 92:3-16).

An antibody comprising the antibody-drug conjugate described in the present patent should preferably maintain the antigen-binding ability it has in its original wild state. Thus, an antibody as described in the context of the present invention is capable of, preferably exclusively, binding to a corresponding antigen. Antigens to which the present invention relates include, for example, tumor-associated antigens (TAA), cell surface receptor proteins and other cell surface molecules, cell survival regulators, cell proliferation regulators, molecules associated with tissue growth and differentiation (where known or predicted to be functional), lymphokines, cytokines, molecules involved in the regulation of cell circulation, molecules involved in angiogenesis, and molecules associated with angiogenesis (where known or predicted to be functional). Tumor-associated factors may correspond to cluster differentiation factors (e.g., CD proteins).

Antibodies described in the present invention for application in an antibody-drug conjugate include, but are not limited to, antibodies targeting cell surface receptors and those targeting tumor-associated antigens. Such tumor-associated antigens are well known to those in the industry, and can be prepared using antibody preparation methods and information that are well known to those in the industry. To develop effective cellular-level targets that could be used in cancer diagnosis and treatment, researchers have sought to identify transmembrane or other tumor-associated peptides.

These targets are specifically expressed on the surface of one or more cancer cells, with little or no expression observed on the surface of one or more non-cancerous cells. Typically, such tumor-associated polypeptides are overexpressed to a greater extent on the surface of cancer cells compared to the surface of non-cancerous cells. The identification of such tumor-associated factors has the potential to greatly enhance the specificity of antibody-based cancer therapy.

Proteins or peptides used in the context of the present patent for the preparation of an antibody-drug conjugate may be any arbitrary peptide or protein that has an affinity for an epitope or corresponding receptor, and they do not necessarily have to belong to the immunoglobulin family. These peptides can be isolated by techniques similar to those used for phage display antibodies (Szardenings, J Recept Signal Transduct Res. 2003: 23 (4): 307-49). The use of peptides from such random peptide libraries may be similar to that of antibodies and antibody fragments. Peptide or protein binding molecules may be bound or linked to a macromolecule or other material, including, but not limited to, albumin, polymers, liposomes, nanoparticles or dendrimers, as long as said binding allows the peptide or protein to retain its antigen binding specificity.

Tumor-associated antigens include antigens that are well known to those in the industry. Nucleic acid and protein sequences corresponding to tumor-associated antigens can be found in publicly available databases, such as Genbank. Tumor-associated antigens relating to antibody targeting include all amino acid sequence variants and homologs having at least 70%, 80%, 85%, 90%, or 95% homology to a sequence identified in the available literature, or having biological properties and characteristics that are identical to a sequence of a tumor-associated antigen identified in the literature.

The term "inhibition" or "inhibition by" refers to a reduction complete elimination of the corresponding detectable amount.

The term "cancer" refers to a physiological condition or disease characterized by unregulated cell growth. "Tumor" includes cancer cells.

The term "autoimmune disease" refers to a disease or disorder that results from the targeting of an individual's own tissues or proteins.

As used herein, the phrase "pharmaceutically acceptable salt" refers to a pharmaceutically acceptable organic or inorganic salt of a compound (e.g., a drug, drug-junction or ligand-junction-drug conjugate). Said compound may contain at least one amino or carboxyl group and may thus form an adduct salt with a corresponding acid or base. Illustrative examples of salts include, but are not limited to: sulfate, trifluoroacetate, citrate, acetate, oxalate, chloride, bromide, iodide, nitrate, hydrogen sulfate, phosphate, acid phosphate, isonicotinic acid salts, lactate, salicylate, acid citrate, tartarate, oleate, tannate, pantothenate, hydrogen tartrate, ascorbate, salicylate, formate, benzoate, glutamate, methanesulfonate, ethanesulfonate, benzenesulfonate, p-toluenesulfonate, potassium salts, sodium salts, etc. Additionally, pharmaceutically acceptable salts have more than one charged atom in their structure. Examples in which multiple charged atoms which are part of a pharmaceutically acceptable salt may have multiple instances of counterbalance. For example, a pharmaceutically acceptable salt may have one or more charged atoms and/or one or more counteracting atoms.

Preferred drugs refer to: cytotoxic drugs used in cancer therapy, including but not limited to, maitansine or maytansinoids, analogs of dolastatin 10, cachymycins, doxorubicins, benzodipyrrole antibiotics (duocarmycins, CC-1065, etc.), pyrrolo[2,1-c][1,4]benzodi-azepines (PBDs) or PBD dimmers and derivatives thereof, amantin or derivatives thereof and camptothecin compounds including camptothecin, hydroxycamptothecin, SN-38, icticam, irinotecan, etc.

On the other hand, viable drugs are not limited to the categories mentioned above, but rather include all drugs that can be used in an antibody-drug conjugate.

In some embodiments, the invention also includes radioisotopes connected via an acidic self-stabilization junction. These include, but are not limited to: $^{3}H$, $^{11}C$, $^{18}F$, $^{32}P$, $^{35}S$, $^{64}Cu$, $^{68}Ga$, $^{86}Y$, $^{99}Tc$, $^{111}In$, $^{123}I$, $^{125}I$, $^{131}I$, $^{133}Xe$, $^{177}Lu$, $^{211}At$ and $^{213}Bi$.

Based on the mechanism of drug release into the cell, as used herein, "linkers" or "antibody-drug conjugate linkers" can be divided into two categories: non-breakable linkers and breakable linkers.

For antibody-drug conjugates containing an unbreakable linker, the mechanism of drug release is as follows: after the conjugate binds to the antigen and is endocytosed, the antibody is enzymatically cleaved in the lysosome, releasing an active molecule consisting of a small molecule drug, a linker, and an antibody amino acid residue. The resulting change in the molecular structure of the drug does not reduce its cytotoxicity, but because the active molecule is charged (due to the amino acid residues), it will be unable to penetrate into neighboring cells. Therefore, said active drug will not be able to kill adjacent tumor cells that do not express the target antigen (antigen-negative cells) (known as the "bystander effect") (Ducry, et al. 2010, Bioconjugate Chem. 21:5-13).

A breakable linker, as the name implies, can break and release the active drug (the small molecule drug itself) in the target cell. Breakable linkers can be divided into two main classes: chemically unstable linkers and enzymatically unstable linkers.

Chemically unstable linkers can be selectively broken due to differences in the properties of plasma and cytoplasm. Such properties include pH, glutathione concentration, etc.

In some embodiments of the present patent, the linker corresponds to a pH-sensitive linker, also commonly referred to as an acid-sensitive linker. Such linkers are relatively stable in the neutral environment of the blood (pH 7.3 to 7.5), but are hydrolyzed within weakly acidic endosomes (pH 5.0 to 6.5) and lysosomes (pH 4.5 to 5.0). Most first-generation antibody-drug couplings employ these types of linkers, with examples including hydrazones, carbonates, acetals, and ketones. Due to the limited plasma stability of acid-sensitive linkers, antibody-drug conjugates based on such linkers typically have a short half-life (2 to 3 days). This short half-life to some extent has limited the use of pH-sensitive linkers in the latest generation of antibody-drug conjugates.

Glutathione-sensitive linkers are also known as disulfide linkers. The corresponding mechanism of drug release is based on the difference between the high intracellular glutathione concentration (millimolar range) and the relatively low glutathione concentration (micromolar range) found in the blood. This is especially true for tumor cells, where low oxygen content leads to increased reductase activity and thus to higher glutathione levels. Disulfide bonds are thermodynamically stable and therefore exhibit good stability in plasma.

Enzyme-unstable linkers, such as peptide linkers, allow for better control of drug release. Peptide linkers can be effectively cleaved by lysosomal proteases such as cathepsin B or fibronectin (increased levels of these enzymes are found in some tumor tissues). This peptide linkage is thought to be very stable in the plasma circulation due to the unsuitable extracellular pH as well as the presence of serum protease inhibitors, ensuring that proteases are usually inactive. Given the high stability of plasma as well as favorable intracellular breakage selectivity and potency, enzyme-unstable linkers are widely used as breakable linkers for antibody-drug conjugates. Typical enzyme-unstable linkers include Val-Cit(vc), Phe-Lys, and others.

A spacer unit is generally embedded between a breakable linker and the active drug, or is itself part of the breakable linker. The mechanism of action of the spacer unit is as follows: when the breakable linker breaks under suitable conditions, the spacer unit spontaneously undergoes structural rearrangement, thus releasing the active drug to which it is attached. Common such spacer units include p-aminobenzyl alcohols (PABs) and β-glucuronides, substituted or unsubstituted ethylenediamines, etc.

The present patent may use the following abbreviations, which should be understood as having the following fixed meanings: Boc: tert-butoxycarbonyl; DCC: dicyclohexylcarbodiimide; DCM: dichloromethane; DIPEA: diisopropylcarbodiimide; DMF: N,N-dimethylformamide; DMAP: 4-(N,N-dimethylamino)pyridine; HATU: (1[Bis(dimethylamino)methylene]-1H-1,2,3-triazolo[4,5-b]pyridinium-3-oxide hexafluorophosphate; HPLC: high performance liquid chromatography; PEG: polyethylene glycol; TFA: trifluoroacetic acid; THF: tetrahydrofuran; PBS: phosphate buffer solution (pH 7.0 to 7.5).

Pharmaceutically acceptable excipients include any carrier, diluent, adjuvant or excipient, such as preservatives and antioxidants, fillers, disintegrants, wetting agents, emulsifiers, suspension agents, solvents, dispersion media, coating agents, antimicrobial and antifungal agents, delayed absorption agents, etc. The use of such media and agents with pharmaceutically active substances is well known in the field. In addition to incompatibility between any conventional medium or reagent with the active ingredient, its use in therapeutic compositions has also been taken into account. As a suitable form of therapeutic combination, supplemental active ingredients can also be incorporated into said composition.

The main advantages of the present invention are as follows:

1. The antibody-drug conjugate having an acidic stabilization junction provided by the present invention can substantially reduce the rate of exchange with albumin sulfhydryl groups in vivo, significantly increasing plasma stability.
2. Due to the incorporation of an acidic group, the acidic stabilization junction provided by the present invention exhibits better water solubility at the molecular level, effectively improving the PK properties of a corresponding antibody-drug conjugate which shows better in vivo efficacy.
3. The antibody-drug conjugate having an acidic stabilization junction provided by the present invention not only provides increased plasma stability, it also improves the PK properties of the final conjugate, and these advantages are able to fully satisfy the demands of higher drug loads, reducing the aggregation of antibody-drug conjugate at a high drug load while also obtaining better efficacy compared with lower drug loads.

In the following section, the invention is described in further detail in conjunction with specific examples, and it should be understood that said examples are used only to illustrate the invention and are not intended to limit the scope of the invention. Test methods for which no specific conditions are specified in the following examples were generally performed under conventional conditions or under the conditions recommended by the manufacturer. Unless otherwise stated, all percentages, proportions, ratios, or portions are given on a weight basis. Unless otherwise defined, all professional and scientific terms used in the following text are intended to have the meanings generally understood by those skilled in the art. In addition, any methods and materials similar or equal to those described may be applied in the methods constituted by the present invention. The preferred methods and materials described in the following text are for demonstration purposes only.

The general procedures employed in the following embodiments of the invention are as follows:

General Procedure A

Following preliminary purification, antibody molecules with a monomer ratio greater than 95% were exchanged into phosphate buffer containing EDTA at a concentration of 10 mg/ml using an ultrafiltration centrifuge tube. TCEP in a molar amount 10-fold that of the antibody was added and the resulting reaction was allowed to proceed for eight hours. The disulfide bonds between the antibody chains were opened and the number of free sulfhydryl groups was determined using the method of Ellman to ascertain whether or not all disulfide bonds were open. Next, payload in a molar amount 10-fold that of the antibody was added and the resulting reaction was allowed to proceed for eight hours. Once the reaction had finished, an ultrafiltration centrifuge tube with a molecular weight cut-off of 30 KDa was used to exchange the solution into PBS and the uncoupled payload was removed.

General Procedure B

Pharmacokinetic Studies

ELISA Method for Detection of Antibodies in Serum: Antibody coating (2 ug/ml) was carried out at 4° C. overnight followed by PBST washing which was repeated three times and 1% BSA+PBST blocking at 37° C. for one hour; serum samples were incubated and washed with PBST three times; detection antibodies (anti-Fc monoclonal antibody or polyclonal antibody [HRP-labelled]) were incubated at 37° C. for one hour washed with PBST three times and developed with TMB, after which 2M $H_2SO_4$ was then used to terminate the reaction and measurements were taken using a microlplate reader.

General Procedure C

Hydrophobic Interaction Chromatography (HIC) Assay

ADC analysis was performed using hydrophobic interaction chromatography (HIC). Elution was performed using 0 to 100% Mobile Phase B (MPB), where Mobile Phase A (MPA) consisted of 1.5 M ammonium sulfate and 0.025 M sodium phosphate, and MPB consisted of 0.025 M sodium phosphate and 25% isopropanol. The sample loading volume was approximately 20 μg, and gradient elution was completed in 15 minutes. 280 nm UV was used for detection, and the stronger the water-transporting sample, the later the peak produced.

General Procedure D

Plasma Stability Studies

A fixed amount of ADC sample was added to human plasma for which human IgG had already been removed, with each ADC tube prepared in triplicate; next, incubation in a 37° C. water bath was performed for 0 hours and 72 hours, after which the ADC sample was removed and 100 μl of Protein A (MabSelect SuRe™ LX Lot: #10221479GE, washed with PBS) was added to each tube; adsorption was then allowed to proceed under agitation on a vertical mixer for two hours, followed by washing and elution to obtain incubated ADC; the plasma stability of each incubated ADC sample was then determined via RP-HPLC.

General Procedure E: Site-Specific Coupling of ADC

Following preliminary purification, antibody molecules with a monomer ratio greater than 95% were exchanged into phosphate buffer containing EDTA at a concentration of 10 mg/ml using an ultrafiltration centrifuge tube. TCEP in a molar amount 10-fold that of the antibody was added and the resulting reaction was allowed to proceed for two hours. Using an ultrafiltration centrifuge tube to exchange the solution into pH 6.5 phosphate buffer, DHAA in a molar amount 10-fold that of the antibody was thereafter added and the resulting reaction was allowed to proceed for two hours. Next, payload in a molar amount 3-fold that of the antibody was added and the resulting reaction was allowed to proceed for four hours. Once the reaction had finished, an ultrafiltration centrifuge tube with a molecular weight cut-off of 30 KDa was used to exchange the solution into PBS and the uncoupled payload was removed to obtain site-specific coupled ADC (DAR=2).

Example 1

Preparation of Compound 1

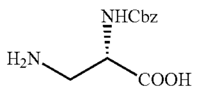

50 g of(S)—N-benzyloxycarbonyl-N'-tert-butoxycarbonyl-2,3-diaminopropionic acid was dissolved in 500 mL of dichloromethane, after which 50 mL of trifluoroacetic acid was added and the reaction solution was stirred at room temperature overnight. After the reaction was complete, the reaction solution was concentrated until dry under reduced pressure, after which ethyl acetate was added to dissolve the resulting solid followed by addition of hexane and stirring to precipitate out solids which were filtered and dried to obtain a solid product weighing 21 g. LC-MS m/z ($ES^+$): 239.1 $(M+H)^+$ Example 2

Preparation of Compound 2

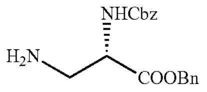

200 mL of benzyl alcohol was added to a reaction flask and thionyl chloride (6.69 mL, 92.4 mmol) was slowly added dropwise in a water bath; once dropwise addition was complete, stirring was performed for one hour followed by batch addition of Compound 1 (20 g, 84 mmol) and once addition was complete the mixture was stirred at room temperature overnight. After the reaction was complete, benzyl alcohol was distilled off via an oil pump under reduced pressure, and the resulting residue was subject to separation using silica gel column chromatography (eluent: dichloromethane:methanol=150:1) to obtain 22 g of product. LC-MS m/z ($ES^+$): 329.1 $(M+H)^+$ Example 3

Preparation of Compound 3

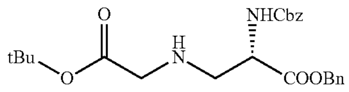

Compound 2 (10 g, 30.4 mmol) was dissolved in 150 mL of acetonitrile, diisopropylethylamine (DIEA, 4.72 mL, 36.58 mmol) was added, and tert-butyl bromoacetate (4.75 g, 24.4 mmol) was added dropwise in an ice water bath; following dropwise addition, the reaction was allowed to proceed for 30 minutes before the reaction mixture was moved to room temperature conditions for further reaction, after which TLC monitoring (developer: DCM:MeOH=10:1) was performed. After the reaction was complete, the solution was concentrated under reduced pressure, and the resulting residue was subject to separation using silica gel column chromatography (eluent: dichloromethane:methanol=100:1) to obtain 5.9 g of product. LC-MS m/z ($ES^+$): 443.3 $(M+H)^+$ Example 4

Preparation of Compound 4

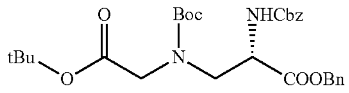

Compound 3 (5.9 g, 13.3 mmol), 30 mL of 1,4-dioxane, and 30 mL of water were added into a reaction flask, followed by addition of DIEA (3.3 mL, 20 mmol) and dropwise addition of Boc anhydride (14.5 g, 66.7 mmol) at room temperature; the resulting reaction solution was yellow, and the reaction was allowed to proceed at room temperature for approximately 3 to 4 hours following dropwise addition after which TLC monitoring (developer: DCM:MeOH=30:1) was performed. After the reaction was complete, dioxane was removed via concentration under reduced pressure and DCM was added to perform an extraction followed by concentration under reduced pressure to obtain a crude yellow oily product; this was then subject to separation using silica gel column chromatography (eluent: dichloromethane:methanol=300:1) to obtain 6.6 g of product. LC-MS m/z ($ES^+$): 443.3 $(M+H)^+$-Boc, 543.2 $(M+H)^+$ Example 5

Preparation of Compound 5

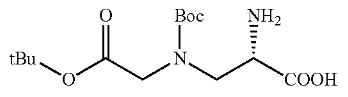

6.6 g of Compound 4 was dissolved in 50 ml of methanol, 1.32 g of 5% Pd/C was added and hydrogen gas exchange was performed two to three times while the mixture was reacted at room temperature and TLC monitoring (developer: DCM:MeOH=5:1) was performed. After the reaction was completed, the reaction solution was filtered and concentrated under reduced pressure at 40° C. to obtain 4.4 g of product which was directly used in the next reaction.

Example 6

Preparation of Compound 6

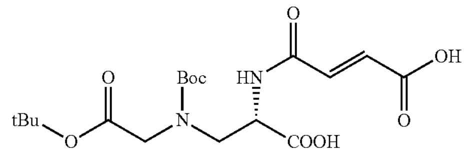 [SMILES: CC(C)(C)OC(=O)CN(C[C@H](NC(=O)/C=C/C(=O)O)C(=O)O)C(=O)OC(C)(C)C]

Compound 5 (4.4 g, 13.8 mmol) was dissolved in 40 mL of glacial acetic acid, maleic anhydride (2.71 g, 27.6 mmol) was added, and the reaction allowed to proceed while stirring was performed at room temperature. The reaction was monitored via TLC (DCM:MeOH=3:1). Once the reaction was complete, the reaction solution was concentrated under reduced pressure and the resulting residue was purified using an HPLC liquid phase.

(Column: YMC-C18, 100 mm×450 mm, 10 μm, acetonitrile/water (0.2% TFA), flow rate 200 mL/min, detection at λ=215 nm)

Solvent A: 0.2% TFA water

Solvent B: Acetonitrile

Gradient: 0 to 10 min, 90% A, 10 to 25 min, 90 to 45% A, 25 to 55 min, 45 to 40% A The fraction with a retention time of 43 min was collected and lyophilized to obtain 1.51 g of a white solid. LC-MS m/z ($ES^+$): 317.9 $(M+H)^+$-Boc, 417.9 $(M+H)^+$ Example 7

Preparation of Compound 7

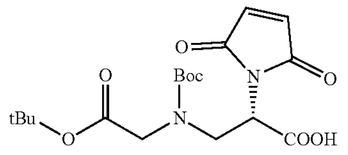 [SMILES: CC(C)(C)OC(=O)CN(C[C@@H](C(=O)O)N1C(=O)C=CC1=O)C(=O)OC(C)(C)C]

Compound 6 (1.2 g, 2.88 mmol) was dissolved in 25 mL of dry toluene and 2.5 mL of DMA solution and triethylamine (1.2 mL, 8.65 mmol) was added (a few dry molecular sieves can be added), nitrogen gas replacement was performed and the mixture was heated to 120° C. while the reaction was monitored via TLC (developer: DCM:MeOH=3:1). After the reaction was complete, the solution was concentrated under reduced pressure using an oil pump, and the resulting residue was subject to separation using silica gel column chromatography (eluent: dichloromethane:methanol from 20:1 to 10:1) to obtain 700 mg of product. LC-MS m/z ($ES^+$): 299.2 $(M+H)^+$-Boc, 399.3 $(M+H)^+$ Example 8

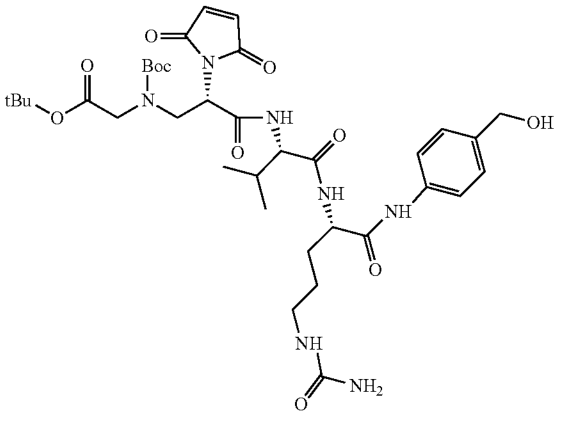 [SMILES: CC(C)[C@H](NC(=O)[C@H](CN(CC(=O)OC(C)(C)C)C(=O)OC(C)(C)C)N1C(=O)C=CC1=O)C(=O)N[C@@H](CCCNC(N)=O)C(=O)Nc1ccc(CO)cc1]

700 mg (1.7 mmol) of Compound 7 was dissolved in 3.5 mL of DMF, after which 531 mg (2.11 mmol) of EEDQ and 733 mg (1.93 mmol) of Val-Cit-PABOH were added and the reaction was allowed to proceed at room temperature. Monitoring was performed via TLC (developer: DCM:MeOH=5:1). After the reaction was complete, the solution was concentrated under reduced pressure using an oil pump at 45° C., and the resulting residue was subject to separation using silica gel column chromatography (eluent: dichloromethane:methanol from 50:1 to 20:1) to obtain 520 mg of product. LC-MS m/z ($ES^+$): 660.3 $(M+H)^+$-Boc, 760.4 $(M+H)^+$ Example 9

Preparation of Compound 9

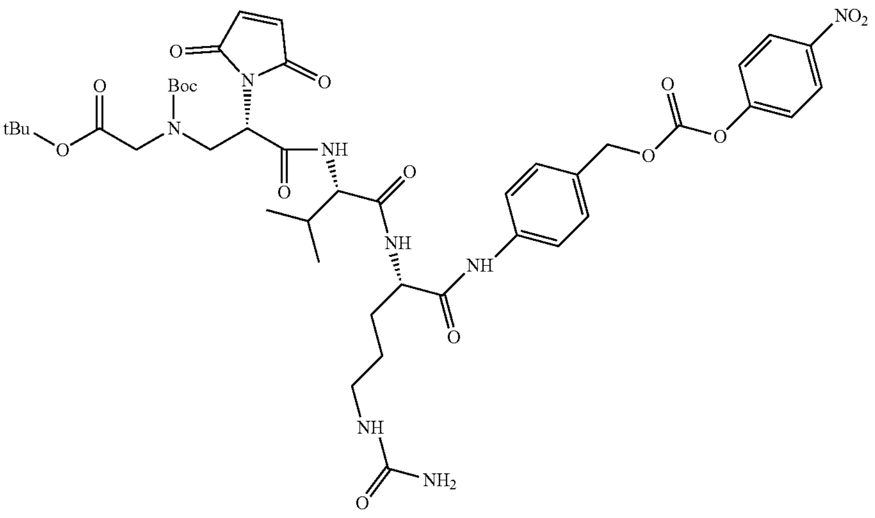 [SMILES: CC(C)[C@H](NC(=O)[C@H](CN(CC(=O)OC(C)(C)C)C(=O)OC(C)(C)C)N1C(=O)C=CC1=O)C(=O)N[C@@H](CCCNC(N)=O)C(=O)Nc1ccc(COC(=O)Oc2ccc([N+](=O)[O-])cc2)cc1]

520 mg (0.685 mmol) of Compound 8 and 1.04 g (3.42 mmol) of NCP were sequentially added to a reaction flask, 10 mL of DMF was added to dissolve the solids and 0.33 mL (2.05 mmol) of DIEA was added after which the reaction was allowed to proceed at room temperature. Monitoring was performed via TLC (developer: DCM:MeOH=5:1). After the reaction was complete, the solution was concentrated under reduced pressure using an oil pump at 45° C., and the resulting residue was subject to separation using silica gel column chromatography (eluent: dichloromethane: methanol=30:1) to obtain 530 mg of product. LC-MS m/z ($ES^+$): 825.3 $(M+H)^+$-Boc, 925.2 $(M+H)^+$ Example 10

Preparation of Compound 10

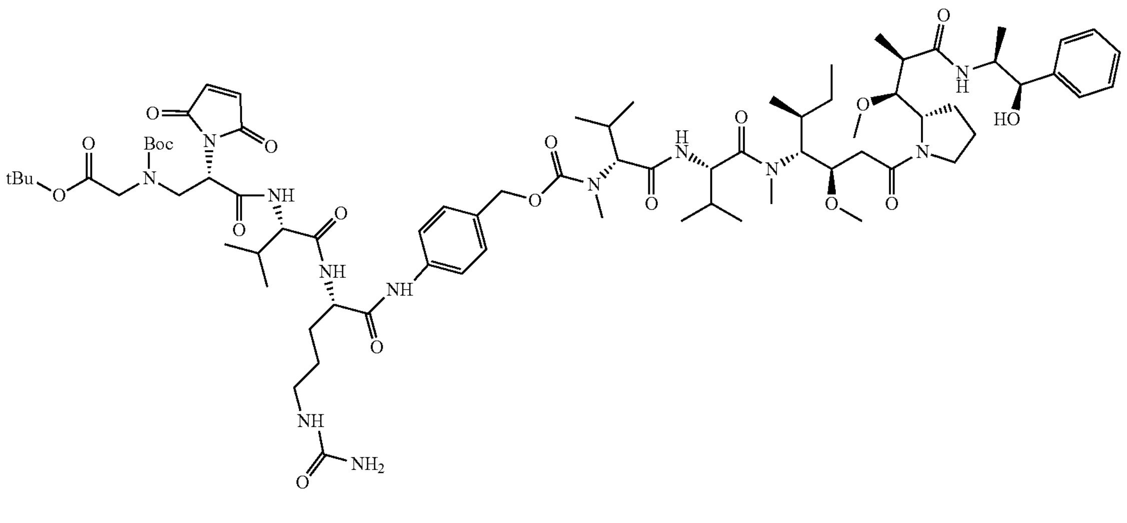 [SMILES: CC[C@H](C)[C@H]([C@@H](CC(=O)N1CCC[C@H]1[C@@H](OC)[C@@H](C)C(=O)N[C@@H](C)[C@H](O)c1ccccc1)OC)N(C)C(=O)[C@@H](NC(=O)[C@@H](C(C)C)N(C)C(=O)OCc1ccc(NC(=O)[C@H](CCCNC(N)=O)NC(=O)[C@@H](NC(=O)[C@H](CN(CC(=O)OC(C)(C)C)C(=O)OC(C)(C)C)N2C(=O)C=CC2=O)C(C)C)cc1)C(C)C]

530 mg (0.57 mmol) of Compound 9 and 13.5 mg (0.1 mol) of HOBT were dissolved in 5 mL of DMF, 0.17 mL (1.04 mmol) of DIEA was added, and, after activation at room temperature for 1 h, 373 mg (0.52 mmol) of MMAE was added and the solution was allowed to react overnight at room temperature. HPLC monitoring showed that the raw starting material MMAE was fully reacted. Purification was performed using an HPLC liquid phase.

(Column: YMC-C18, 50 mm×450 mm, 10 μm, acetonitrile/water (0.2% TFA), flow rate 50 mL/min, detection at λ=205 nm)

Solvent A: 0.2% TFA water

Solvent B: Acetonitrile

Gradient: 0 to 10 min, 90% A, 10 to 25 min, 90 to 45% A, 25 to 55 min, 45 to 40% A The fraction with a retention time of 34 min was collected and lyophilized to obtain 200 mg of product; LC-MS m/z ($ES^+$): 1503.2 $(M+H)^+$ Example 11

Preparation of Compound 11

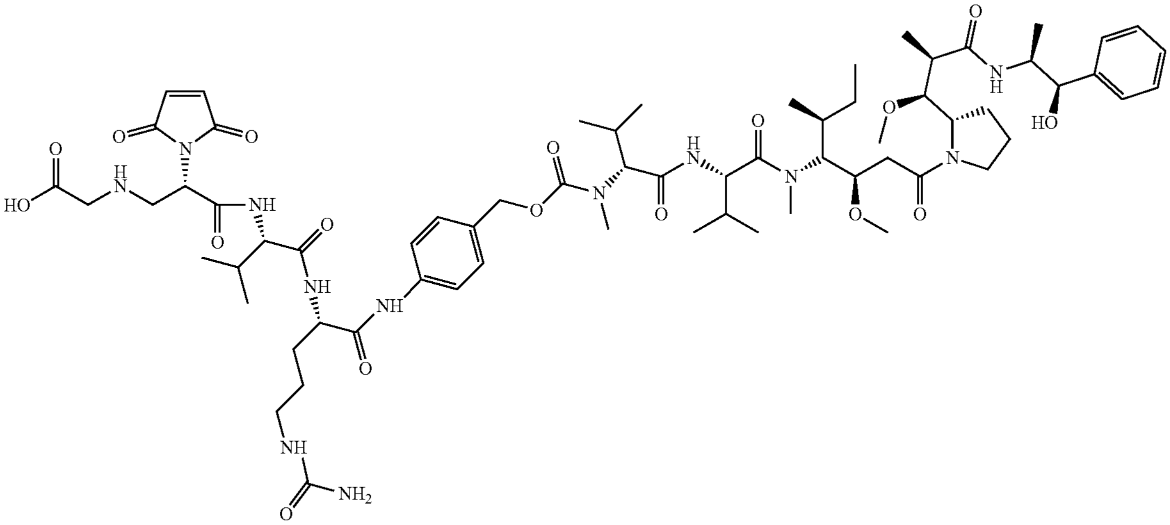

70 mg of Compound 10 was dissolved in 10 mL of dry dichloromethane, 4 mL of trifluoroacetic acid was added, and the reaction was allowed to proceed at room temperature for one hour, followed by purification via HPLC.

(Column: YMC-C18, 30 mm×450 mm, 10 μm, acetonitrile/water (0.2% TFA), flow rate 25 mL/min, detection at λ=205 nm)

Solvent A: 0.2% TFA water

Solvent B: Acetonitrile

Gradient: 0 to 10 min, 95% A, 10 to 30 min, 95 to 80% A, 30 to 50 min, 80 to 50% A The fraction with a retention time of 33 min was collected and lyophilized to obtain 34 mg of product; LC-MS m/z ($ES^+$): 1347.8 $(M+H)^+$ Example 12

Preparation of Compound 12

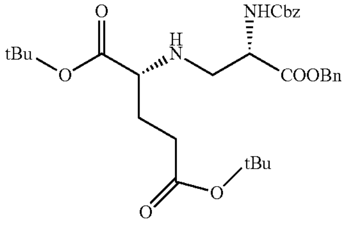

Di-tert-butyl L-glutamate (8 g, 30.8 mmol) was dissolved in 150 mL of acetonitrile, DIEA (6 mL, 37 mmol) was added, and 2-bromo-N-(benzyloxycarbonyl)-L-alanine benzyl ester (10.2 g, 26.1 mmol) was added dropwise in an ice water bath; following dropwise addition, the reaction was allowed to proceed for 40 minutes after which the reaction solution was moved to room temperature conditions and allowed to react further while TLC monitoring (developer: DCM:MeOH=10:1) was performed. After the reaction was complete, the solution was concentrated under reduced pressure, and the resulting residue was subject to separation using silica gel column chromatography (eluent: dichloromethane:methanol=100:1) to obtain 8.1 g of product. LC-MS m/z ($ES^+$): 571.2 $(M+H)^+$ Example 13

Preparation of Compound 13

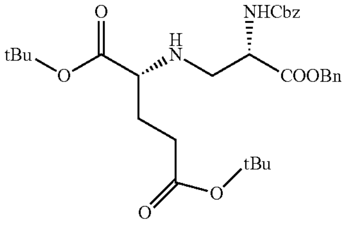

8.1 g of Compound 12 (14.2 mmol), 50 mL of 1,4-dioxane, and 50 mL of water were added into a reaction flask, followed by addition of 3.5 mL of DIEA (21.3 mmol) and dropwise addition of 14.5 g of Boc anhydride (66.7 mmol) at room temperature; the resulting reaction solution was yellow, and the reaction was allowed to run to completion at room temperature during which TLC monitoring (developer: DCM:MeOH=30:1) was performed. After the reaction was complete, dioxane was removed via concentration under reduced pressure and DCM was added to perform an extraction followed by concentration under reduced pressure to obtain a crude yellow oily product; this was then subject to separation using silica gel column chromatography (eluent: dichloromethane:methanol=300:1) to obtain 8.55 g of product. LC-MS m/z ($ES^+$): 471.1 $(M+H)^+$-Boc, 571.3 $(M+H)^+$ Example 14

Preparation of Compound 14

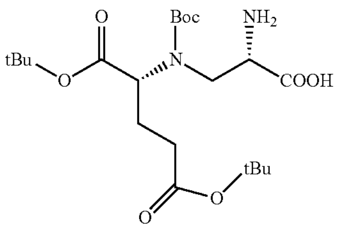 [SMILES: CC(C)(C)OC(=O)CC[C@H](C(=O)OC(C)(C)C)N(C[C@H](N)C(=O)O)C(=O)OC(C)(C)C]

8.5 g of Compound 13 was dissolved in 70 ml of methanol, 1.7 g of 5% Pd/C was added and hydrogen gas exchange was performed two to three times while the mixture was reacted at room temperature and TLC monitoring (developer: DCM:MeOH=5:1) was performed. After the reaction was completed, the reaction solution was filtered and concentrated under reduced pressure at 40° C. to obtain 5 g of product which was directly used in the next reaction. 20

Example 15

Preparation of Compound 15

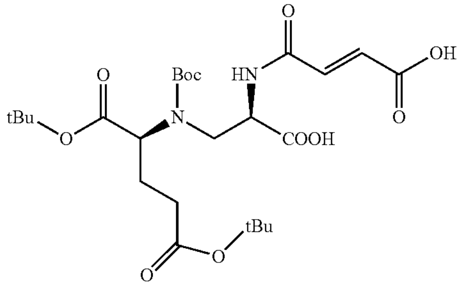 [SMILES: CC(C)(C)OC(=O)CC[C@@H](C(=O)OC(C)(C)C)N(C[C@@H](NC(=O)/C=C/C(=O)O)C(=O)O)C(=O)OC(C)(C)C]

5 g (11.2 mmol) of Compound 14 was dissolved in 40 mL of glacial acetic acid, 2.19 g (22.4 mmol) of maleic anhydride was added, and the reaction was allowed to proceed under stirring at room temperature. The reaction was monitored via TLC (DCM:MeOH=3:1). Once the reaction was complete, the reaction solution was concentrated under reduced pressure and the resulting residue was purified using an HPLC liquid phase.

(Column: YMC-C18, 100 mm×450 mm, 10 μm, acetonitrile/water (0.2% TFA), flow rate 200 mL/min, detection at λ=215 nm)

Solvent A: 0.2% TFA water

Solvent B: Acetonitrile

Gradient: 0 to 10 min, 90% A, 10 to 25 min, 90 to 45% A, 25 to 55 min, 45 to 40% A The fraction with a retention time of 48 min was collected and lyophilized to obtain 2.3 g of product. LC-MS m/z ($ES^+$): 445.2 $(M+H)^+$-Boc, 545.3 $(M+H)^+$ Example 16

Preparation of Compound 16

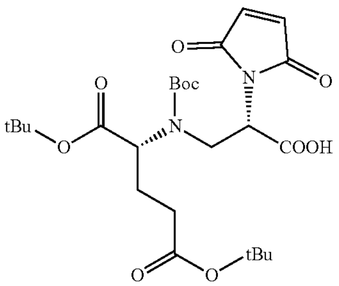 [SMILES: CC(C)(C)OC(=O)CC[C@H](C(=O)OC(C)(C)C)N(C[C@@H](C(=O)O)N1C(=O)C=CC1=O)C(=O)OC(C)(C)C]

2 g of Compound 15 (2.88 mmol) was dissolved in 25 mL of dry toluene and 2.5 mL of DMA solution and 1.58 mL of triethylamine (11.4 mmol) was added, nitrogen gas replacement was performed and the mixture was heated to 120° C. while the reaction was monitored via TLC (developer: DCM:MeOH=3:1). After the reaction was complete, the solution was concentrated under reduced pressure using an oil pump, and the resulting residue was subject to separation using silica gel column chromatography (eluent: dichloromethane:methanol from 20:1 to 10:1) to obtain 1.19 g of product; LC-MS m/z ($ES^+$): 427.1 $(M+H)^+$-Boc, 527.3 $(M+H)^+$.

Example 17

Preparation of Compound 17

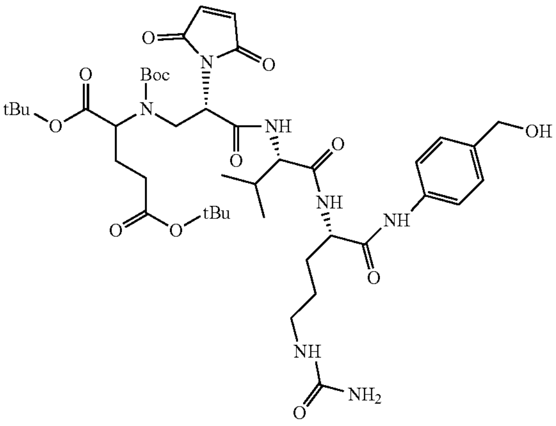 [SMILES: CC(C)[C@H](NC(=O)[C@H](CN(C(=O)OC(C)(C)C)C(CCC(=O)OC(C)(C)C)C(=O)OC(C)(C)C)N1C(=O)C=CC1=O)C(=O)N[C@@H](CCCNC(N)=O)C(=O)Nc1ccc(CO)cc1]

1.19 g (1.7 mmol) of Compound 16 was dissolved in 3.5 mL of DMF, after which 531 mg (2.11 mmol) of EEDQ and 733 mg (1.93 mmol) of Val-Cit-PABOH were added and the reaction was allowed to proceed at room temperature. Monitoring was performed via TLC (developer: DCM:MeOH=5:1). After the reaction was complete, the solution was concentrated under reduced pressure using an oil pump at 45° C., and the resulting residue was subject to separation using silica gel column chromatography (eluent: dichloromethane:methanol from 50:1 to 25:1) to obtain 753 mg of product. LC-MS m/z ($ES^+$): 788.5 $(M+H)^+$-Boc, 888.4 $(M+H)^+$ Example 18

Preparation of Compound 18

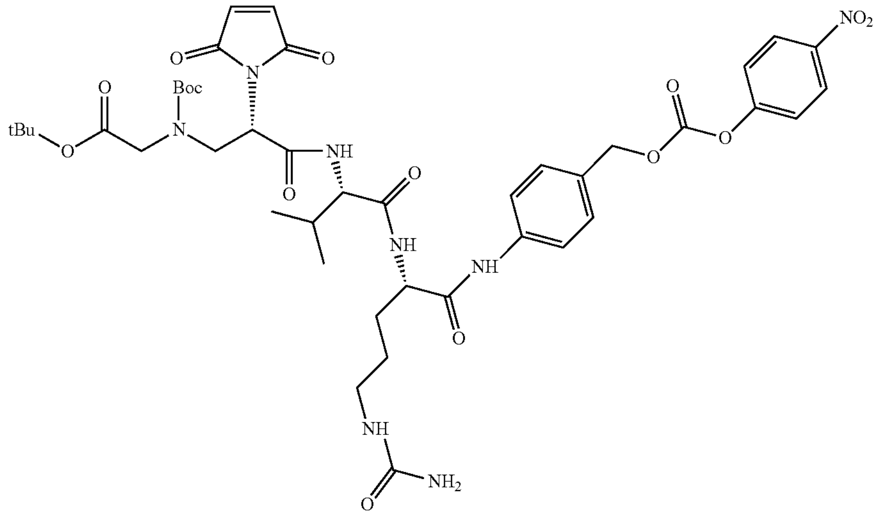 [SMILES: CC(C)[C@H](NC(=O)[C@H](CN(CC(=O)OC(C)(C)C)C(=O)OC(C)(C)C)N1C(=O)C=CC1=O)C(=O)N[C@@H](CCCNC(N)=O)C(=O)Nc1ccc(COC(=O)Oc2ccc([N+](=O)[O-])cc2)cc1]

753 mg (0.849 mmol) of Compound 17 and 1.28 g (4.24 mmol) of NCP were sequentially added to a reaction flask, 15 mL of DMF was added to dissolve the solids and 0.35 mL (2.55 mmol) of DIEA was added after which the reaction was allowed to proceed at room temperature. Monitoring was performed via TLC (developer: DCM:MeOH=5:1). After the reaction was complete, the solution was concentrated under reduced pressure using an oil pump at 45° C., and the resulting residue was subject to separation using silica gel column chromatography (eluent: dichloromethane: methanol=25:1) to obtain 762 mg of product. LC-MS m/z ($ES^+$): 1053.6 $(M+H)^+$ Example 19

Preparation of Compound 19

762 mg (0.71 mmol) of Compound 18 and 13.5 mg (0.1 mol) of HOBT were dissolved in 8 mL of DMF, 0.23 mL (1.42 mmol) of DIEA was added, and, after activation at room temperature for 1 h, 463 mg (0.645 mmol) of MMAE was added and the solution was allowed to react overnight at room temperature. HPLC monitoring showed that the raw starting material MMAE was fully reacted. Purification was performed using an HPLC liquid phase.

(Column: YMC-C18, 100 mm×450 mm, 10 μm, acetonitrile/water (0.2% TFA), flow rate 200 mL/min, detection at λ=215 nm)

Solvent A: 0.2% TFA water

Solvent B: Acetonitrile

Gradient: 0 to 10 min, 90% A, 10 to 25 min, 90 to 45% A, 25 to 55 min, 45 to 40% A The fraction with a retention time of 30 min was collected and lyophilized to obtain 300 mg of product. LC-MS m/z ($ES^+$): 1631.6 $(M+H)^+$

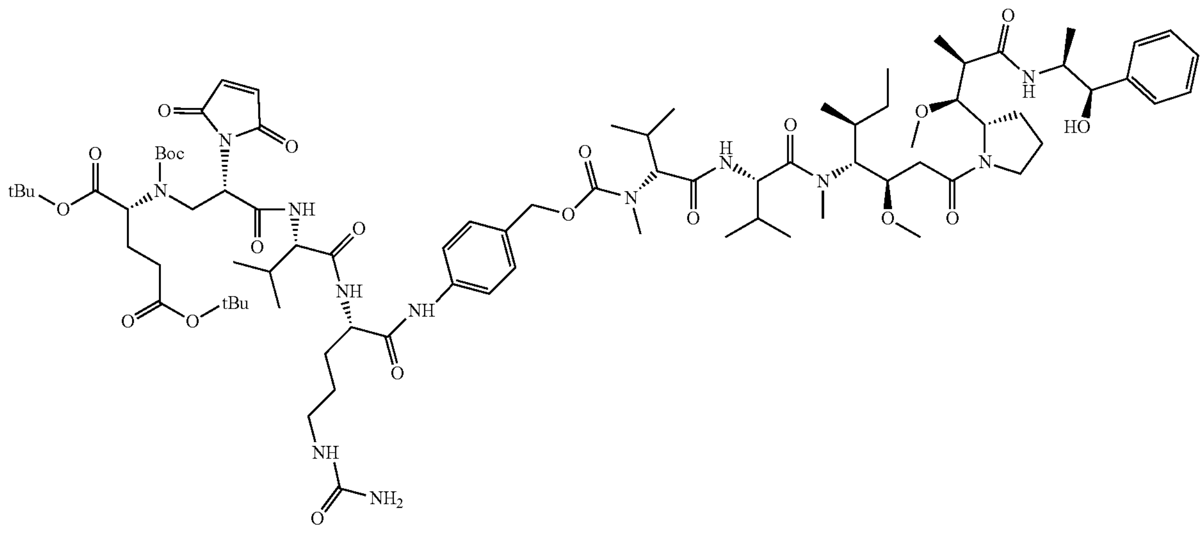

Example 20

Preparation of Compound 20

Preparation of Compound 20

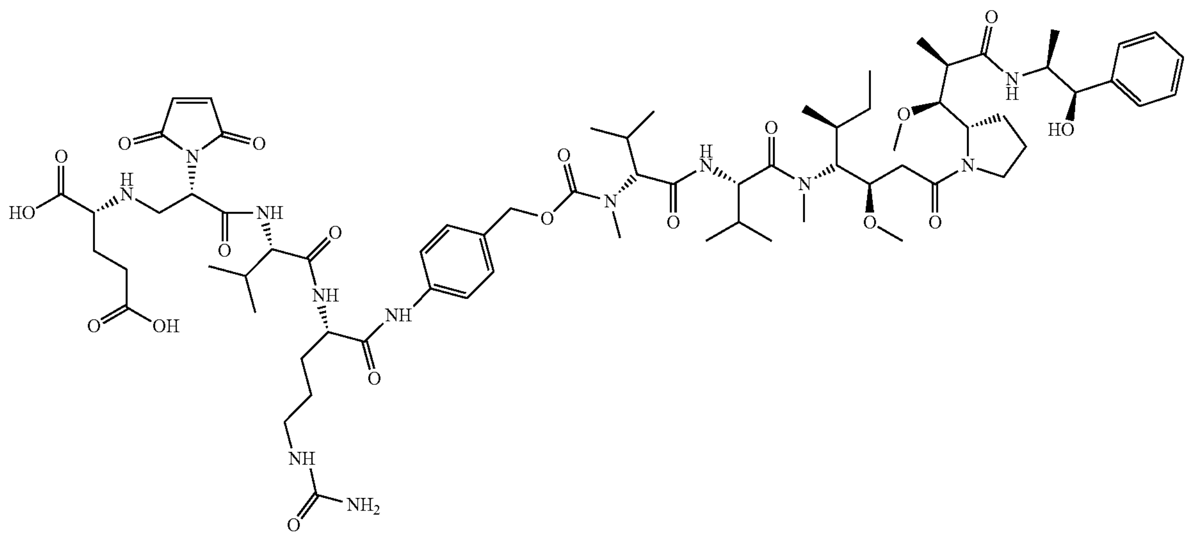

100 mg of Compound 19 was dissolved in 10 mL of dry dichloromethane, 4 mL of trifluoroacetic acid was added, and the reaction was allowed to proceed at room temperature for one hour, followed by purification via HPLC.

(Column: YMC-C18, 30 mm×450 mm, 10 μm, acetonitrile/water (0.2% TFA), flow rate 25 mL/min, detection at λ=215 nm)

Solvent A: 0.2% TFA water

Solvent B: Acetonitrile

Gradient: 0 to 10 min, 95% A, 10 to 25 min, 95 to 80% A, 25 to 55 min, 80 to 55% A The fraction with a retention time of 30 min was collected and lyophilized to obtain 45 mg of product. LC-MS m/z ($ES^+$): 1419.1 $(M+H)^+$

Examples 21 Through 29

Synthesis of Compounds 21 through 29

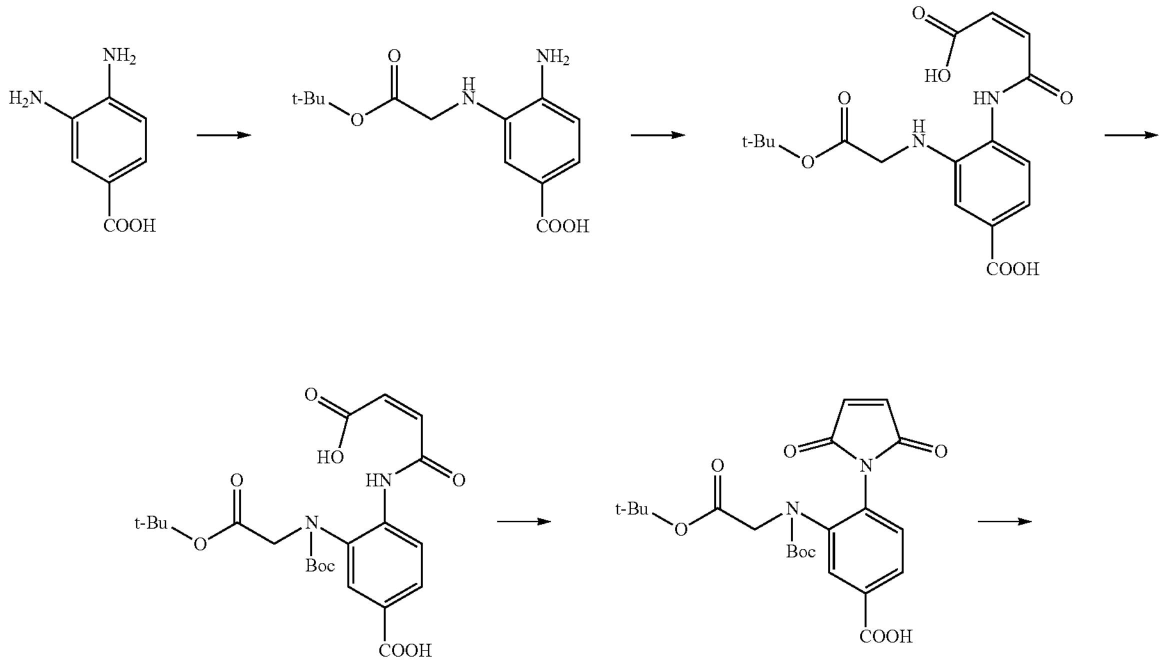

-continued
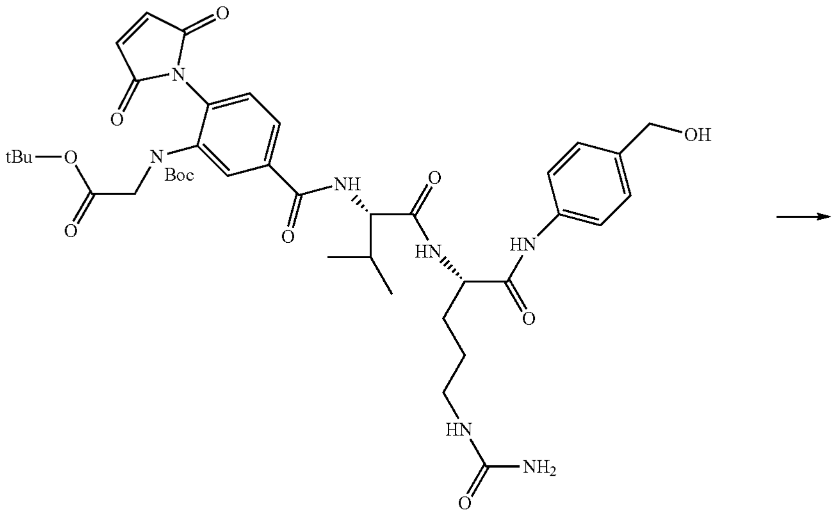
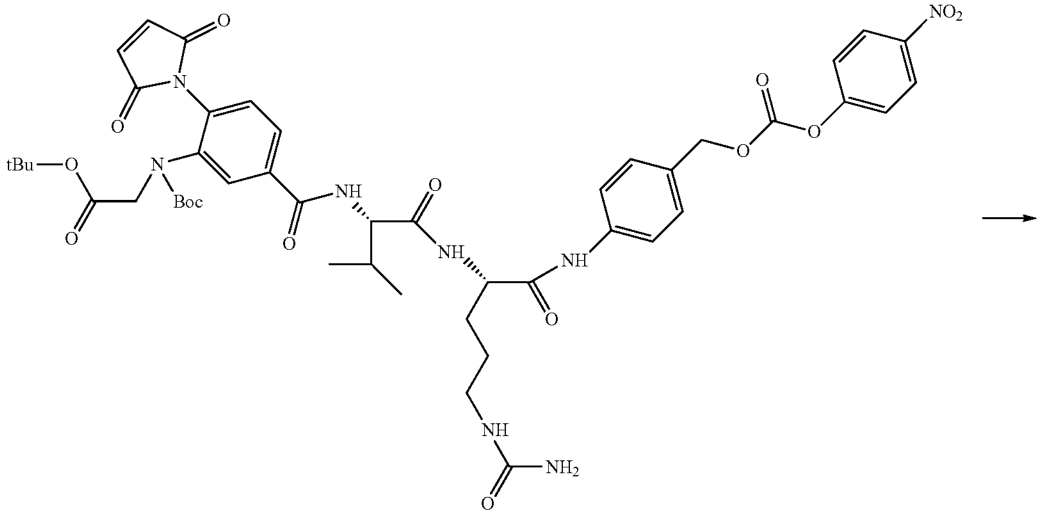
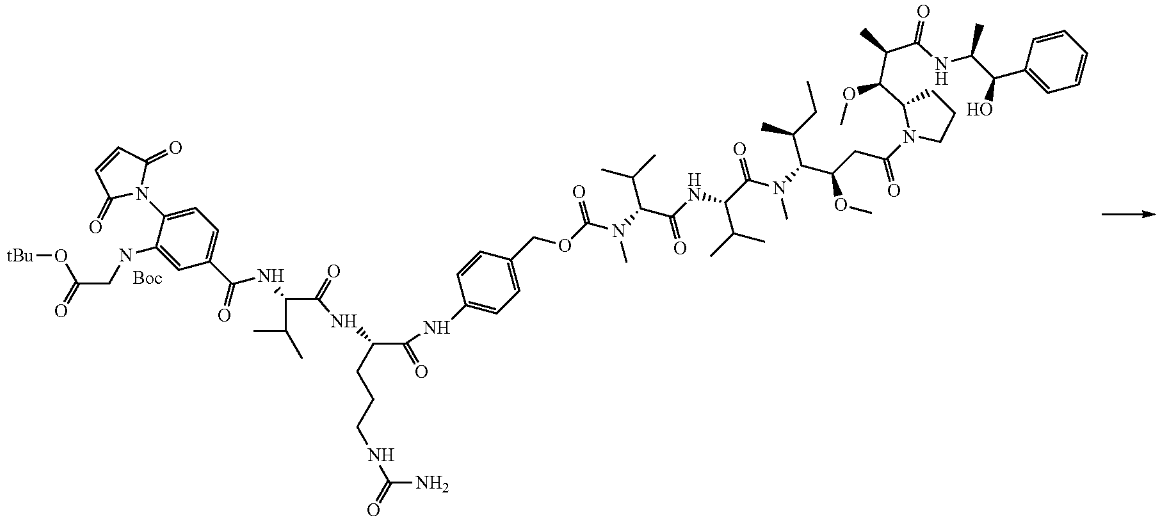

-continued

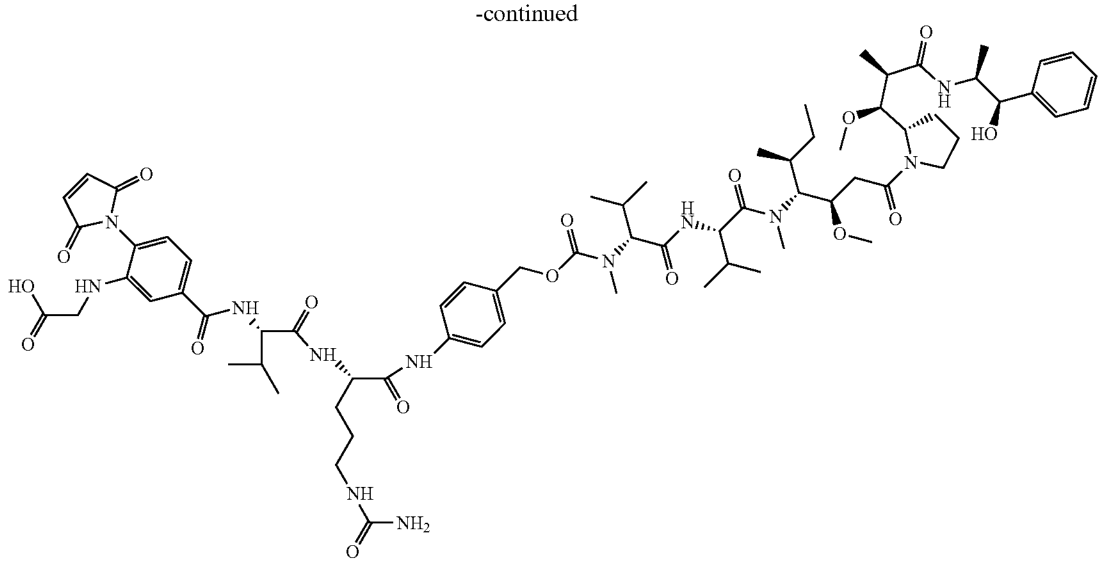

Example 21

Preparation of Compound 21

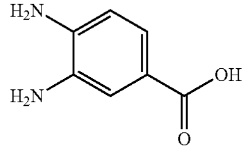

15 g of 3-nitro-4 aminobenzoic acid was dissolved in 100 ml of methanol, 3 g of 5% Pd/C was added and hydrogenation was performed at atmospheric pressure for five hours, followed by filtration; the resulting filter cake was washed twice with methanol, further concentrated until dry at room temperature under high vacuum and directly used in the next reaction without further purification.

Example 22

Preparation of Compound 22

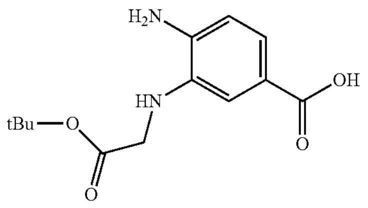 [SMILES: CC(C)(C)OC(=O)CNc1cc(C(=O)O)ccc1N]

3,4-diaminobenzoic acid (10 g, 65.7 mmol) was dissolved in 100 mL DMF, potassium carbonate powder (13.6 g, 98.55 mol) and potassium iodide (2.2 g, 1.31 mmol) were added, and tert-bromoacetic acid was added dropwise under nitrogen gas, after which butyl ester (12.8 g, 65.7 mol) was added dropwise while the reaction was allowed to proceed at room temperature. Monitoring was performed via TLC (developer: DCM:MeOH=10:1). After the reaction was complete, water was added, an ethyl acetate extraction was performed and the extract was combined with organic phase; thereafter, washing with saturated brine, followed by anhydrous sodium sulfate drying and filtration were performed and the solution was concentrated under reduced pressure, and the resulting residue was subject to separation using silica gel column chromatography purification (eluent: dichloromethane:methanol=150:1 to 100:1) to obtain 3.46 g of product. LC-MS m/z (ES$^+$): 267.4 $(M+H)^+$; HNMR: 7.51-7.53, dd, 1H: 7.44-7.45, d, 1H: 6.66-6.69, d, 1H; 4.69, s, 2H: 1.49, s, 9H.

Example 23

Preparation of Compound 23

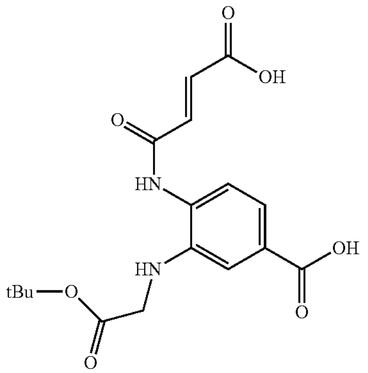 [SMILES: CC(C)(C)OC(=O)CNc1cc(C(=O)O)ccc1NC(=O)/C=C/C(=O)O]

3 g (11.2 mmol) of Compound 22, 15 mL of glacial acetic acid, and maleic anhydride (0.55 g, 5.6 mmol) water were added to a reaction flask, and the resulting reaction was allowed to proceed at room temperature and monitored via HPLC. Once the reaction was complete, concentration under reduced pressure was carried out to remove the glacial acetic acid and purification was carried out. (Column: YMC-C18, 100 mm×450 mm, 10 μm, acetonitrile/water (0.2% TFA), flow rate 200 mL/min, detection at λ=214 nm)

Solvent A: 0.2% TFA water

Solvent B: Acetonitrile

Gradient: 0 to 5 min 80% A, 5 to 35 min, 80 to 65% A, 35 to 45 min, 65 to 60% A, the fraction showing a 37 to 42 min retention time was collected and lyophilized to obtain 2 g of product. LC-MS m/z ($ES^+$): 365.4 $(M+H)^+$, 309.3 $(M+H)^+$-tBu. HNMR: 10.48, s, 1H; 7.41-7.44, dd, 1H; 7.35-7.36, d, 1H; 6.92, s, 2H; 6.70-6.72, d, 1H; 4.68, s, 2H; 1.42, s, 9H.

Example 24

Preparation of Compound 24

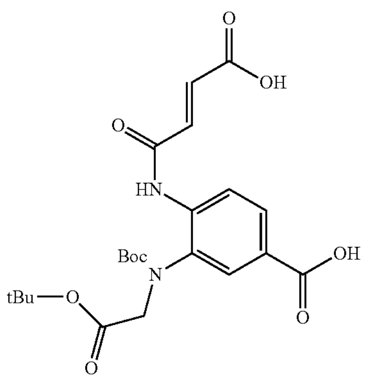 [SMILES: CC(C)(C)OC(=O)CNc1cc(C(=O)O)ccc1NC(=O)/C=C/C(=O)O]

Compound 23 (2 g, 5.49 mmol) was dissolved in 30 ml of THF, and Boc anhydride (1.44 g, 6.59 mmol), DMAP (1.32 g, 10.9 mmol) and DIEA (1.8 mL, 10.98 mmol) and the reaction was allowed to proceed at room temperature. Monitoring was performed via TLC (developer: DCM: MeOH=10:1). After the reaction was complete, the solution was subject to separation using silica gel column chromatography (eluent: dichloromethane:methanol=100:1 to 20:1) to obtain 2.2 g of product. LC-MS m/z ($ES^+$); 365.4 $(M+H)^+$-Boc HNMR: 10.50, s, 1H; 7.46-7.48, dd, 1H; 7.41-7.42, d, 1H; 6.95, s, 2H; 6.73-6.75, d, 1H; 4.69, s, 2H; 1.48, s, 9H; 1.40, s, 9H.

Example 25

Preparation of Compound 25

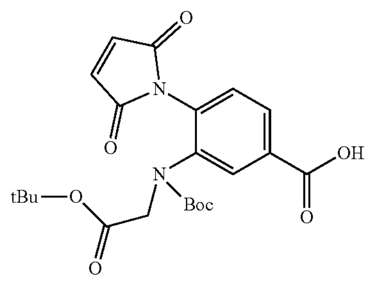 [SMILES: CC(C)(C)OC(=O)CN(C(=O)OC(C)(C)C)c1cc(C(=O)O)ccc1N1C(=O)C=CC1=O]

4 g (4.31 mmol) of Compound 24 was dissolved in 15 mL of toluene and 2 mL of DMA, triethylamine (1.2 mL, 8.62 mmol) was added, and the resulting reaction was allowed to proceed at 120° C. The reaction was monitored via TLC (DCM:MeOH=10:1). After the reaction was complete, the solution was concentrated under reduced pressure, and the resulting residue was subject to separation using silica gel column chromatography purification (eluent: dichloromethane:methanol from 100:1 to 50:1) to obtain 1.63 g of product; LC-MS m/z ($ES^+$): 347.4 $(M+H)^+$-Boc HNMR: 7.50-7.51, dd, 1H; 7.43-7.44, d, 1H; 6.97, s, 2H; 6.75-6.77, d, 1H; 4.67, s, 2H; 1.48, s, 9H; 1.40, s, 9H.

Example 26

Preparation of Compound 26

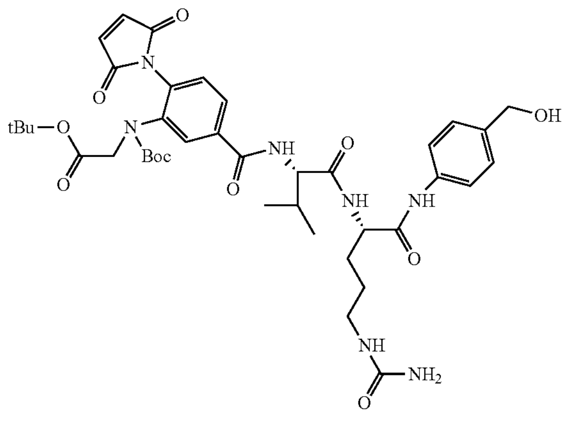 [SMILES: CC(C)[C@H](NC(=O)c1ccc(N2C(=O)C=CC2=O)c(N(CC(=O)OC(C)(C)C)C(=O)OC(C)(C)C)c1)C(=O)N[C@@H](CCCNC(N)=O)C(=O)Nc1ccc(CO)cc1]

1.6 g (3.58 mmol) of Compound 25 was dissolved in 10 mL of DMF, after which 1.77 g (7.17 mmol) of EEDQ and 2.98 g (7.89 mmol) of Val-Cit-PABOH were added and the reaction was allowed to proceed at room temperature. Monitoring was performed via TLC (developer: DCM: MeOH=10:1). After the reaction was complete, the solution was concentrated under reduced pressure using an oil pump at 45° C., and the resulting residue was subject to separation using silica gel column chromatography (eluent: dichloromethane:methanol from 100:1 to 25:1) to obtain 2.1 g of product. LC-MS m/z ($ES^+$): 709.8 $(M+H)^+$-Boc, 809.7 $(M+H)^+$.

Example 27

Preparation of Compound 27

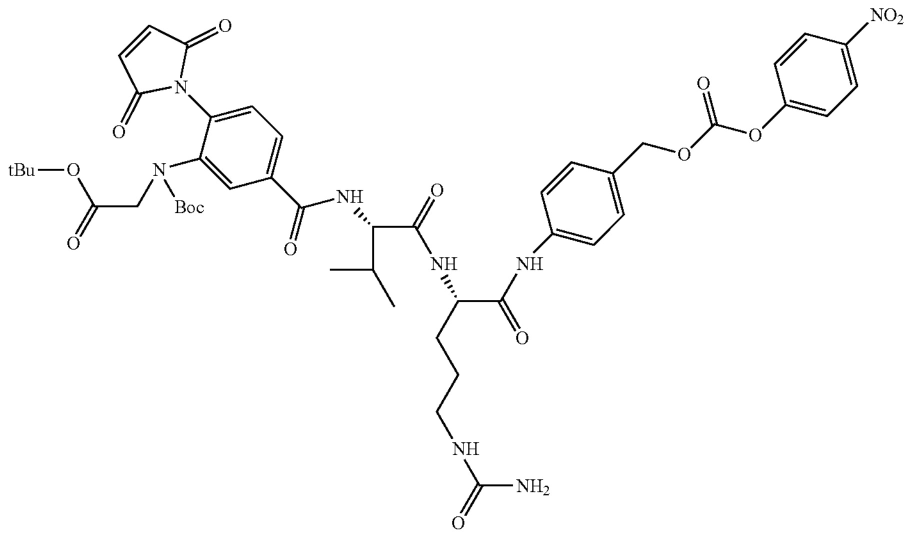 [SMILES: CC(C)[C@H](NC(=O)c1ccc(N2C(=O)C=CC2=O)c(N(CC(=O)OC(C)(C)C)C(=O)OC(C)(C)C)c1)C(=O)N[C@@H](CCCNC(N)=O)C(=O)Nc1ccc(COC(=O)Oc2ccc([N+](=O)[O-])cc2)cc1]

2 g (2.47 mmol) of Compound 26 and 3.71 g (12.3 mmol) of NCP were sequentially added to a reaction flask, 20 mL of DMF was added to dissolve the solids and 1.2 mL (7.41 mmol) of DIEA was added after which the reaction was allowed to proceed at room temperature. Monitoring was performed via TLC (developer: DCM:MeOH=15:1). After the reaction was complete, the solution was concentrated under reduced pressure using an oil pump at 45° C., and the resulting residue was subject to separation using silica gel column chromatography (eluent: dichloromethane:methanol=100:1) to obtain 2.1 g of product. LC-MS m/z (ES$^+$): 973.3 $(M+H)^+$ Example 28

Preparation of Compound 28

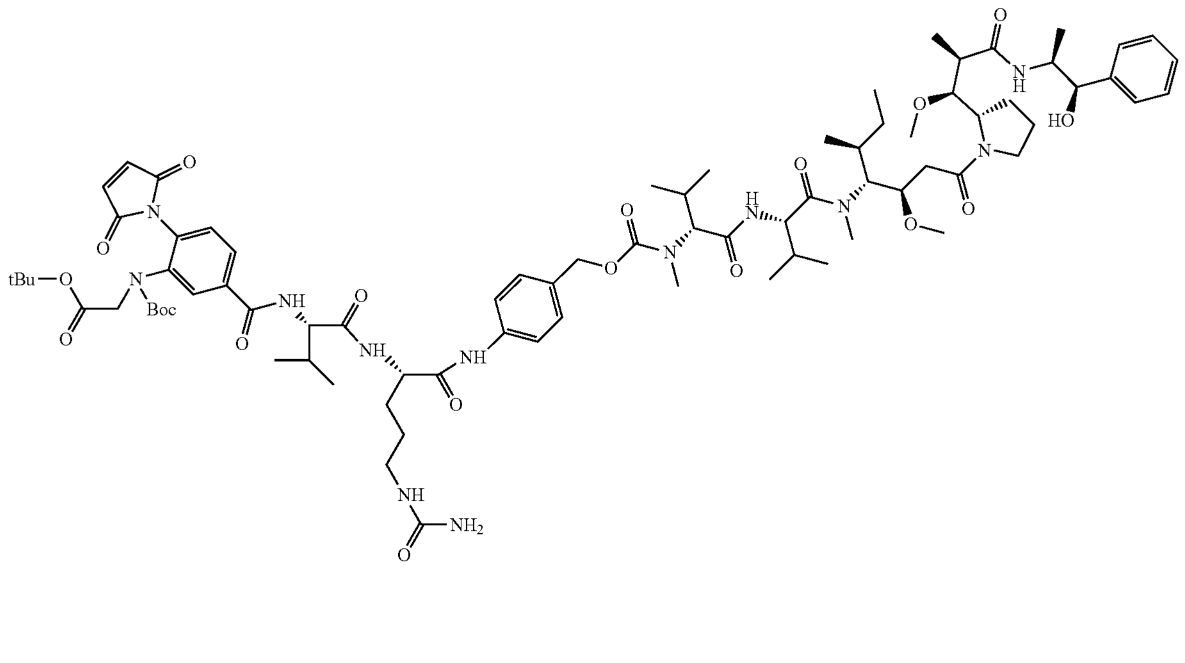

1 g (1 mmol) of Compound 27 and 13.5 mg (0.1 mol) of HOBT were dissolved in 8 mL of DMF, 0.33 mL (2 mmol) of DIEA was added, and, after activation at room temperature for 1 h, 646 mg (0.9 mmol) of MMAE was added and the solution was allowed to react overnight at room temperature. HPLC monitoring showed that the raw starting material MMAE was fully reacted. Purification was performed using an HPLC liquid phase.

(Column: YMC-C18, 100 mm×450 mm, 10 μm, acetonitrile/water (0.2% TFA), flow rate 200 mL/min, detection at λ=214 nm)

Solvent A: 0.2% TFA water

Solvent B: Acetonitrile

Gradient: 0 to 10 min, 90% A, 10 to 25 min, 90 to 45% A, 25 to 55 min, 45 to 40% A The fraction with a retention time of 30 min was collected and lyophilized to obtain 560 mg of product. LC-MS m/z ($ES^+$): 1551.7 $(M+H)^+$ Example 29

Preparation of Compound 29

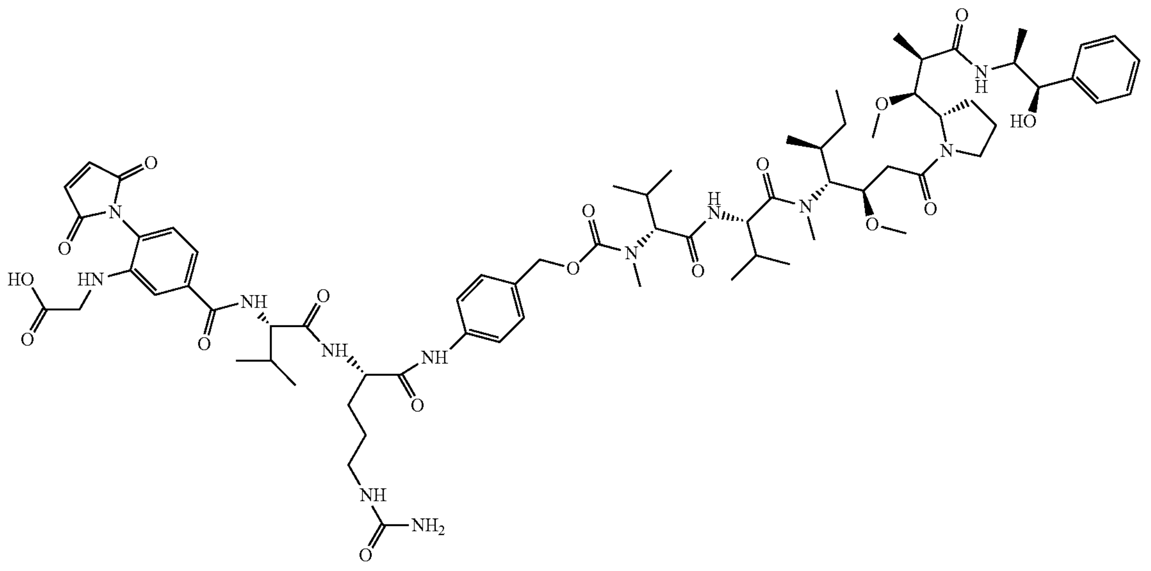

100 mg of Compound 28 was dissolved in 10 mL of dry dichloromethane, 4 mL of trifluoroacetic acid was added, and the reaction was allowed to proceed at room temperature for two hours, followed by purification via HPLC.

(Column: YMC-C18, 30 mm×450 mm, 10 μm, acetonitrile/water (0.2% TFA), flow rate 25 mL/min, detection at λ=214 nm)

Solvent A: 0.2% TFA water

Solvent B: Acetonitrile

Gradient: 0 to 10 min, 95% A, 10 to 25 min, 95 to 80% A, 25 to 55 min, 80 to 55% A The fraction with a retention time of 30 min was collected and lyophilized to obtain 45 mg of product. LC-MS m/z ($ES^+$): 1395.7 $(M+H)^+$ Examples 30 Through 39

Synthesis of Compounds 30 through 39

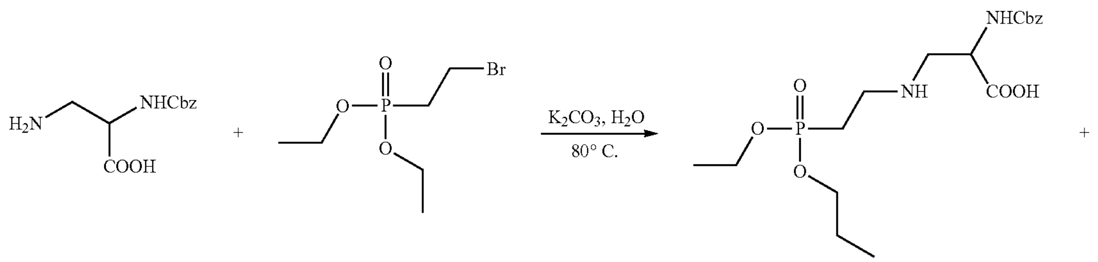

30

-continued
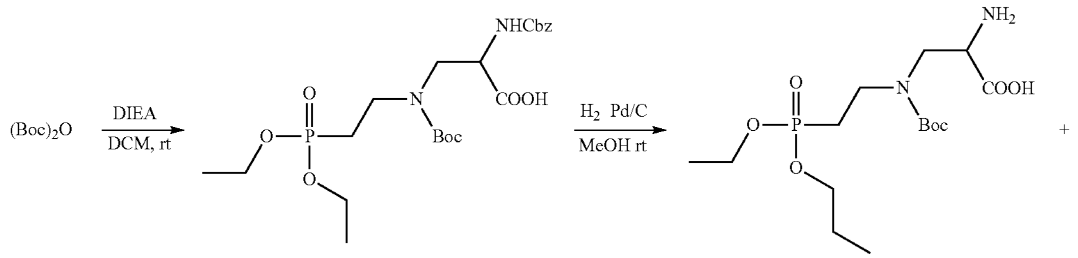
31 32
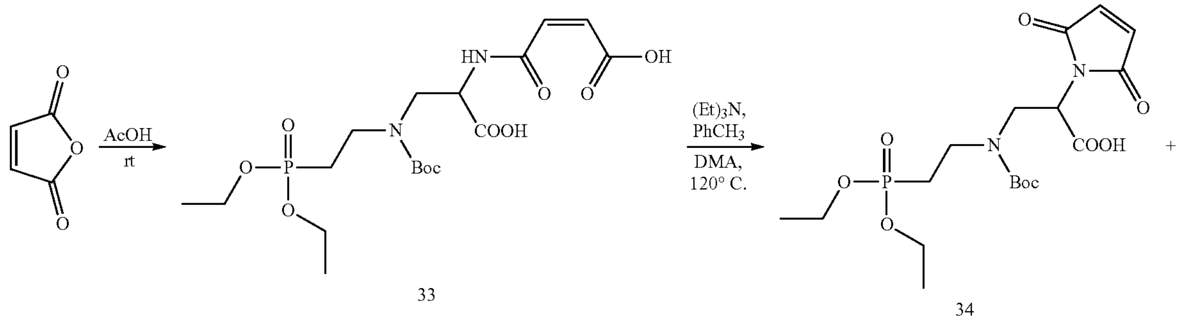
33 34
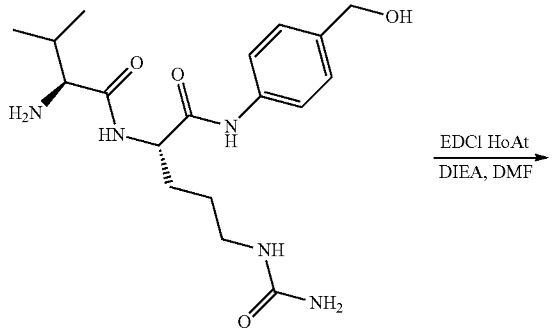
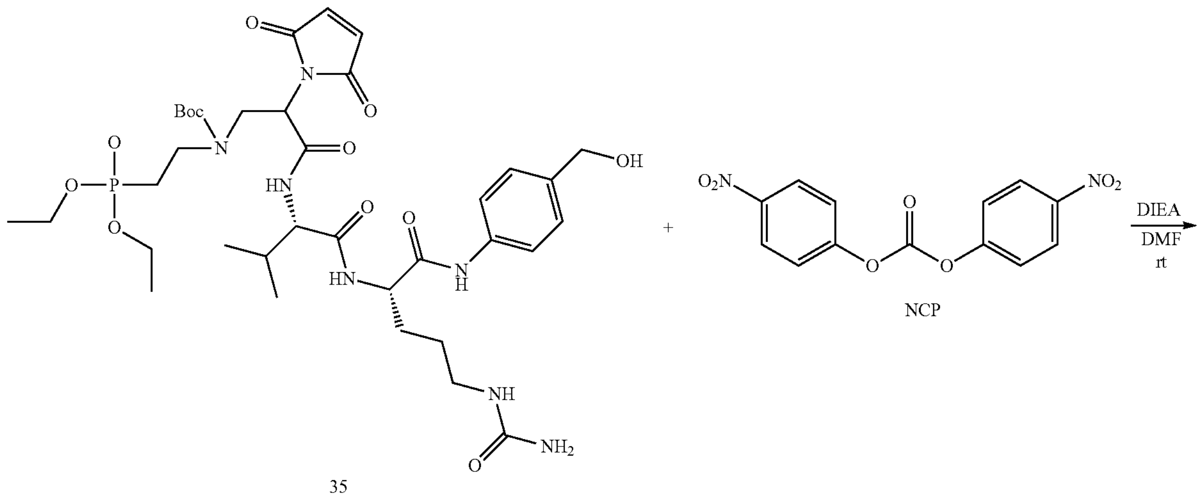
NCP
35

-continued
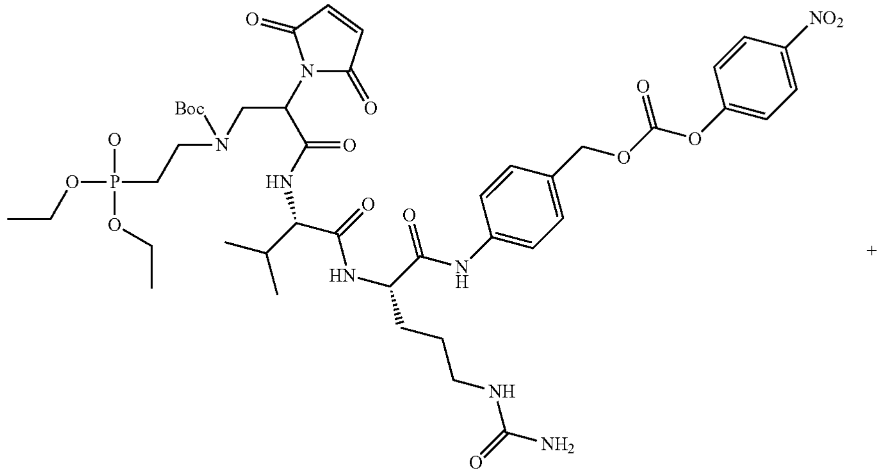
36
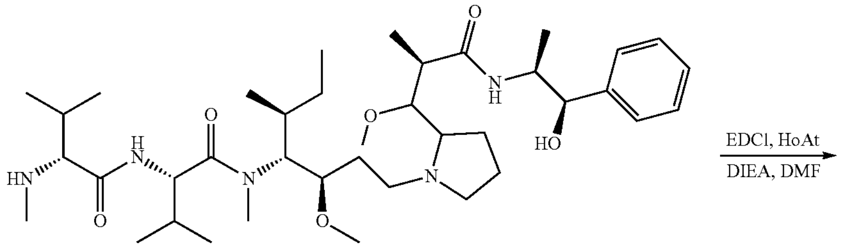
MMAE
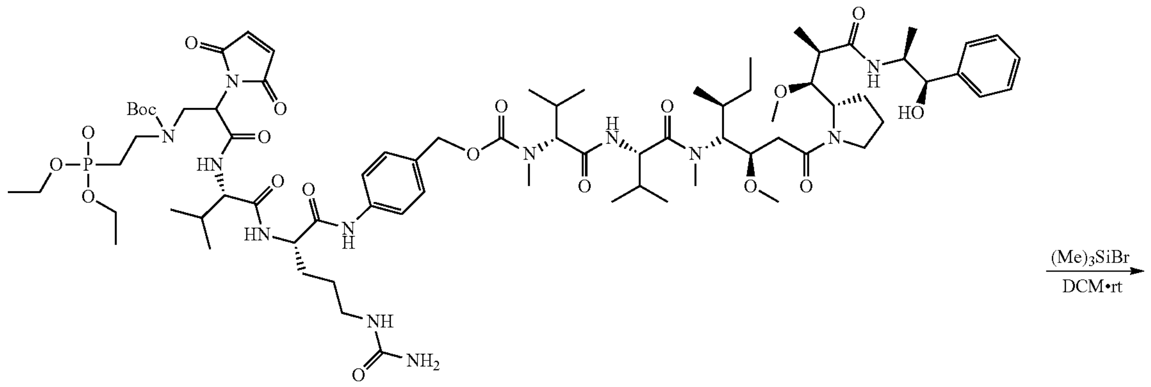
37
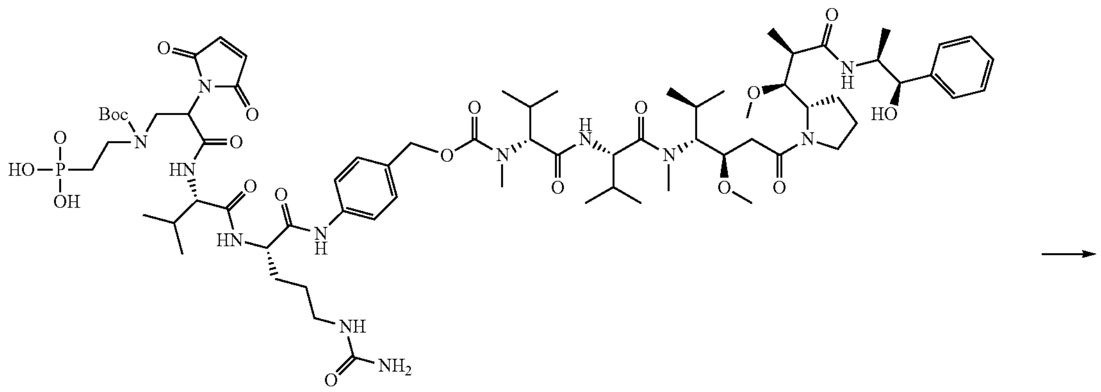
38

-continued

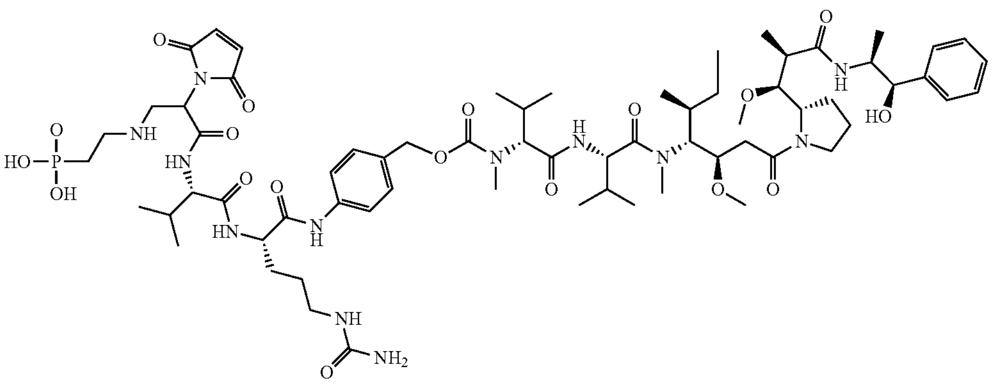

39

Example 30

Preparation of Compound 30

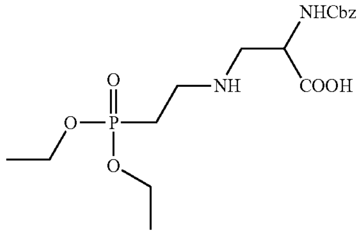 [SMILES: CCOP(=O)(CCNCC(NC(=O)OCc1ccccc1)C(=O)O)OCC]

Using a 500 ml round bottom flask, potassium carbonate (24.7 g, 179.24 mmol) was dissolved in 220 ml of pure water, after which(S)-3-amino-2-(benzyloxycarbonylamino) propionic acid (16 g, 67.16 mmol) was added and the mixture was stirred to almost complete dissolution; next, 2-bromoethyl diethyl phosphate (10.98 g, 44.81 mmol) was added and after addition was complete, the mixture was placed in an oil bath at 80° C. and stirred for six hours until the reaction was complete. The reaction liquid was purified using an HPLC liquid phase. (Column: YMC-C18, 100 mm×450 mm, 10 μm, acetonitrile/water (0.2% TFA), flow rate 200 mL/min, detection at λ=214 nm)

Solvent A: 0.2% TFA water

Solvent B: Acetonitrile

Gradient: 0 to 10 min, 5 to 15% B, 10 to 15 min, 15% B, 15 to 25 min, 15 to 20% B, 25 to 50 min, 20 to 30% B, 50 to 55 min, 30 to 50% B, 55 to 65 min, 50 to 90% B. The fraction with a retention time of 42 to 49 min was collected and lyophilized to obtain 8.38 g of a colorless oily product, with a yield of 46.5%, 1H NMR data ($CDCl_3$, 400 MHz): 7.39-7.28 (m, 5H), 6.54-6.41 (m, 1H), 5.12-5.01 (m, 2H), 4.63-4.53 (m, 1H), 4.16-4.03 (m, 4H), 3.48-3.36 (m, 2H), 3.35-3.25 (m, 2H), 2.35-2.23 (m, 2H), 1.29 (t, J=6.8 Hz, 6H); LCMS $[M+H]^+$ m/z 403.3 (calcd for $C_{17}H_{27}N_2O_7P$, 402.16).

Example 31

Preparation of Compound 31

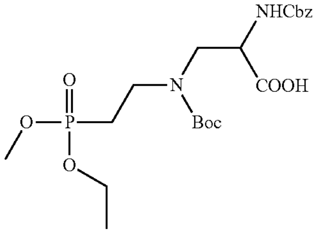 [SMILES: CCOP(=O)(CCN(CC(NC(=O)OCc1ccccc1)C(=O)O)C(=O)OC(C)(C)C)OC]

In a 100 ml three-necked flask, Compound 30 (8.3 g, 20.85 mmol) was dissolved using 50 ml of dichloromethane solvent and the solution was placed in a low temperature reactor set to 0° C. under nitrogen gas, after which DIEA base (6.7 g, 52.11 mmol) was added dropwise with stirring and Boc anhydride (5.0 g, 22.935 mmol) was added dropwise over half an hour; once dropwise addition was complete, the mixture was moved to room temperature and stirred for 2 hours and TLC monitoring was performed until the reaction was complete (developer: DCM:MeOH=4:1). Post-Processing: Water was added to the reaction solution to wash it three times, the organic phase was dried over anhydrous sodium sulfate and concentrated under reduced pressure, and the resulting residue was purified via HPLC. (Column: YMC-C18, 100 mm×450 mm, 10 μm, acetonitrile/water (0.2% TFA), flow rate 200 mL/min, detection at 2=214 nm)

Solvent A: 0.2% TFA water

Solvent B: Acetonitrile

Gradient: 0 min, 40% B, 0 to 10 min, 40% B, 10 to 20 min, 40 to 45% B, 20 to 30 min, 45% B, 30 to 45 min, 45 to 80% B, 45 to 50 min, 80 to 95% B. The fraction with a retention time of 26 to 29.5 min was collected and lyophilized to obtain 4.02 g of a colorless oily liquid, with a yield of 38.3%. 1H NMR data ($CDCl_3$, 400 MHz): 7.36-7.28 (m, 5H), 5.09 (s, 2H), 4.63-4.43 (m, 1H), 4 . . . 14-4.01 (m, 4H), 3.92-3.65 (m, 2H), 3.61-3.29 (m, 2H), 2.34-1.95 (m, 2H), 1.45 (s, 9H), 1.36-1.22 (m, 6H); LCMS $[M+H]^+$ m/z 503.4 (calcd for $C_{22}H_3N_2O_9P$, 502.21).

Example 32

Preparation of Compound 32

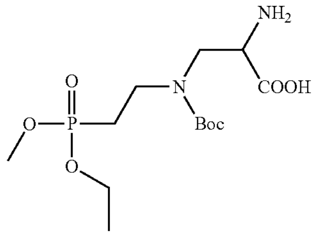 [SMILES: CCOP(=O)(CCN(CC(N)C(=O)O)C(=O)OC(C)(C)C)OC]

In a 150 ml round bottom flask, 50 ml of methanol was used to dissolve Compound 31 (4.0 g, 8.0 mmol) after which 800 mg of Pd/C (containing 5% Pd) was added and hydrogen gas was exchanged, after which the reaction solution was stirred at room temperature for four hours; TLC monitoring (developer: DCM:MeOH=4:1) was performed until the reaction was complete and the reaction was stopped. Organic membrane filtration was used to remove palladium carbon and concentration under reduced pressed was performed, yielding a residue that was directly fed into the next step without any need for purification. LCMS $[M+H]^+$ m/z 369.4 (calcd for $C_{14}H_{29}N_2O_7P$, 368.17).

Example 33

Preparation of Compound 33

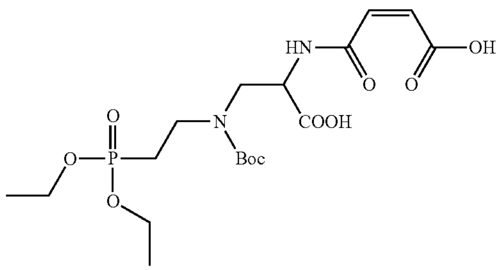 [SMILES: CCOP(=O)(CCN(CC(NC(=O)/C=C\C(=O)O)C(=O)O)C(=O)OC(C)(C)C)OCC]

In a 100 ml round bottom flask, 30 ml of glacial acetic acid was added to dissolve unpurified Compound 32, after which maleic anhydride (1.57 g, 16.0 mmol) was added under stirring and the reaction was allowed to proceed under stirring at room temperature overnight. The reaction was stopped the next day, and the glacial acetic acid was removed via concentration under reduced pressure with an oil pump at 45° C.; the resulting residue was then purified via HPLC. (Column: YMC-C18, 100 mm×450 mm, 10 μm, acetonitrile/water (0.2% TFA), flow rate 200 mL/min, detection at λ=214 nm)

Solvent A: 0.2% TFA water

Solvent B: Acetonitrile

Gradient: 0 min, 5% B, 0 to 10 min, 5 to 15% B, 10 to 20 min, 15 to 30% B, 20 to 35 min, 30 to 55% B, 35 to 45 min, 55% B, 45 to 55 min, 55 to 80% B, 55 to 60 min, 80 to 98% B. The fraction with a retention time of 25 to 26.5 min was collected and lyophilized to obtain 3.35 g of an oily substance, for a two-step yield of 90%. 1H NMR data ($CDCl_3$, 400 MHz): 6.40 (d, J=12 Hz, 1H), 6.35 (d, J=12 Hz, 1H), 4.96 to 4.82 (m, 1H), 4.19-3.99 (m, 4H), 3.98-3.61 (m, 2H), 3.60-3.36 (m, 2H), 2.22-2.00 (m, 2H), 1.45 (s, 9H), 1.33 (t, J=7.0 Hz, 3H), 1.32 (t, J=7.0 Hz, 3H); LCMS $[M+H]^+$ m/z 467.3 (calcd for $C_{18}H_{31}N_2O_{10}P$, 466.17).

Example 34

Preparation of Compound 34

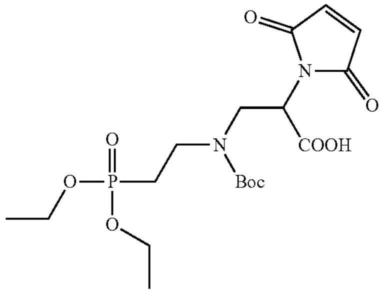 [SMILES: CCOP(=O)(CCN(CC(C(=O)O)N1C(=O)C=CC1=O)C(=O)OC(C)(C)C)OCC]

In a 100 ml round bottom flask, Compound 33 (3.3 g, 7.07 mmol) was dissolved with 40 ml of toluene and 4 ml of DMA under stirring, after which triethylamine (2.1 g, 21.2 mmol) was added, a water trap and reflux condenser were installed and the reaction was allowed to proceed under reflux conditions and stirring at 120° C. for 3 hours until TLC monitoring showed that the reaction was complete (developer: DCM:MeOH=4:1). Post-Processing: The reaction solution was concentrated under reduced pressure at 45° C. to remove toluene, and the resulting residue was purified via HPLC. (Column: YMC-C18, 100 mm×450 mm, 10 μm, acetonitrile/water (0.2% TFA), flow rate 200 mL/min, detection at λ=214 nm)

Solvent A: 0.2% TFA water

Solvent B: Acetonitrile

Gradient: 0 min, 5% B, 0 to 10 min, 5 to 15% B, 10 to 20 min, 15 to 30% B, 20 to 35 min, 30 to 55% B, 35 to 45 min, 55% B, 45 to 55 min, 55 to 80% B, 55 to 60 min, 80 to 98% B. The fraction with a retention time of 27 to 29 min was collected and lyophilized to obtain 2.12 g of a white powdery solid (which rapidly absorbed moisture from the air to become a viscous oil), with a yield of 67%. LCMS $[M+H]^+$ m/z 449.3 (calcd for $C_{18}H_{29}N_2O_9P$, 448.16).

Example 35

Preparation of Compound 35

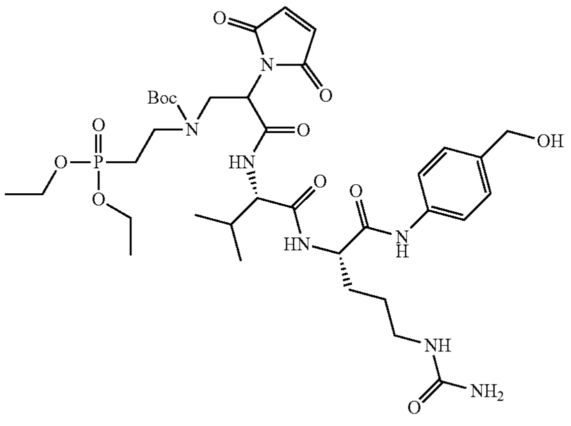 [SMILES: CCOP(=O)(CCN(CC(C(=O)N[C@H](C(=O)N[C@@H](CCCNC(N)=O)C(=O)Nc1ccc(CO)cc1)C(C)C)N1C(=O)C=CC1=O)C(=O)OC(C)(C)C)OCC]

A 100 ml round-bottomed flask containing Compound 34 (2.1 g, 4.69 mmol) was drained using an oil pump, 20 ml of dry DMF was added and the resulting mixture was stirred to complete dissolution; next, DIEA (1.8 g, 14.07 mmol) was added, followed by EDCI (1.81 g, 9.38 mmol) and HoAt (1.28 g, 9.38 mmol), and the activated compound was stirred at room temperature for five and a half hours, after which Compound 6 (2.66 g, 7.03 mmol) was added, and the reaction was allowed to proceed at room temperature overnight before it was stopped the next day. Post-Processing: DMF solvent was removed by concentration under reduced pressure at 45° C. using an oil pump and the resulting residue was purified using column chromatography (eluent: dichloromethane:methanol=20:1 to 10:1 to 5:1) to obtain 1.01 g of a white powdery solid, with a yield of 26.6%. LCMS $[M+H]^+$ m/z 810.4 (calcd for $C_{36}H_{56}N_7O_{12}P$, 809.37).

Example 36

Preparation of Compound 36

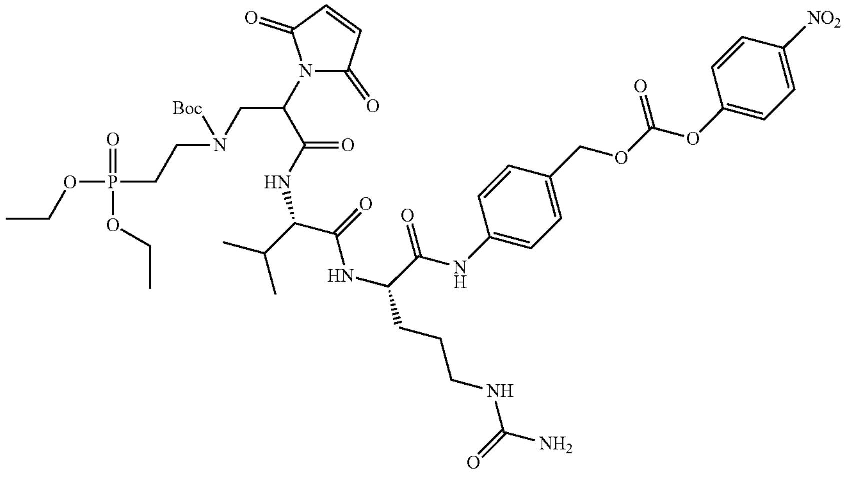 [SMILES: CCOP(=O)(CCN(CC(C(=O)N[C@H](C(=O)N[C@@H](CCCNC(N)=O)C(=O)Nc1ccc(COC(=O)Oc2ccc([N+](=O)[O-])cc2)cc1)C(C)C)N1C(=O)C=CC1=O)C(=O)OC(C)(C)C)OCC]

In a 50 ml round-bottom flask, 15 ml of dry DMF was used to dissolve Compound 35 (1.0 g, 1.24 mmol) under stirring, after which DIEA (961 mg, 7.44 mmol) and NPC (1.88 g, 6.2 mmol) were added and the reaction mixture was allowed to react at room temperature overnight under stirring; on the morning of the next day, TLC monitoring showed that the reaction was complete (developer: dichloromethane:methanol=5:1) and the reaction was stopped. Post-Processing: The reaction solution was concentrated under reduced pressure using an oil pump at 45° C., and the resulting residue was purified via thin-layer chromatography (developer: dichloromethane:methanol=6:1) to obtain 1.02 g of a white powdery solid, with a yield of 84.5%. LCMS $[M+H]^+$ m/z 975.3 (calcd for $C_{43}H_{59}N_8O_{16}P$, 974.38).

Example 37

Preparation of Compound 37

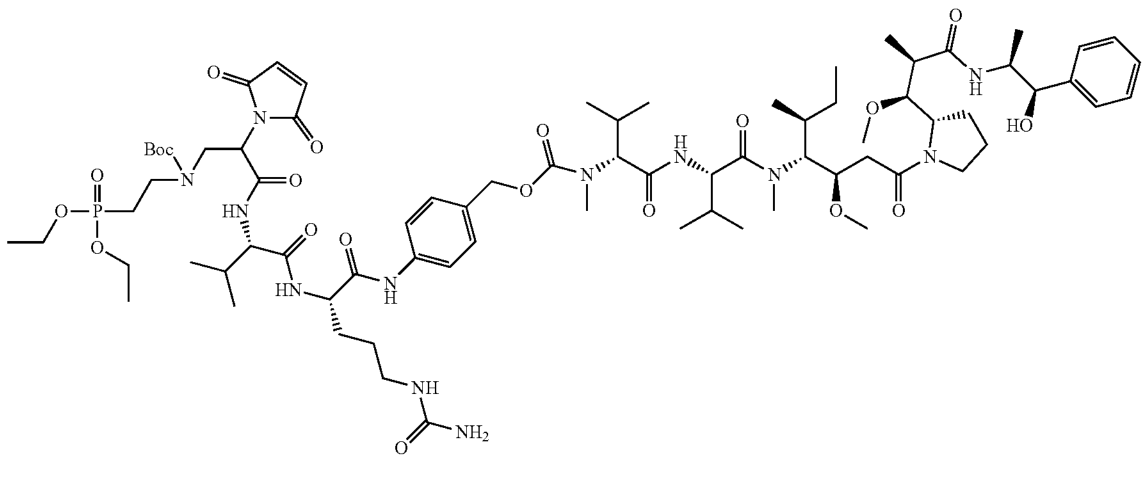

In a 100 ml round bottom flask, 10 ml of dry DMF was used to dissolve Compound 36 (1.0 g, 1.03 mmol) after which HoBt (28 mg, 0.21 mmol) and DIEA (266 mg, 2.06 mmol) were added and the resulting reaction was allowed to proceed under stirring for half an hour; next, MMAE (740 mg, 1.03 mmol) was added, and the reaction was allowed to proceed overnight at room temperature. Post-Processing: The reaction solution was purified via liquid phase preparation. (Column: YMC-C18, 50 mm×450 mm, 10 μm, acetonitrile/water (0.2% TFA), flow rate 50 mL/min, detection at λ=214 nm)

Solvent A: 0.2% TFA water

Solvent B: Acetonitrile

Gradient: 0 min, 5% B, 0 to 10 min, 5 to 15% B, 10 to 20 min, 15 to 30% B, 20 to 35 min, 30 to 55% B, 35 to 45 min, 55 to 70% B, 45 to 55 min, 70% B, 55 to 60 min, 70 to 98% B.

The fraction with a retention time of 38 to 40 min was collected and lyophilized to obtain 320 mg of a white powdery solid, with a yield of 20%. LCMS $[M+H]^+$ m/z 1553.8 (calcd for $C_{76}H_{121}N_{12}O_{20}P$, 1552.85).

Example 38

Preparation of Compound 38

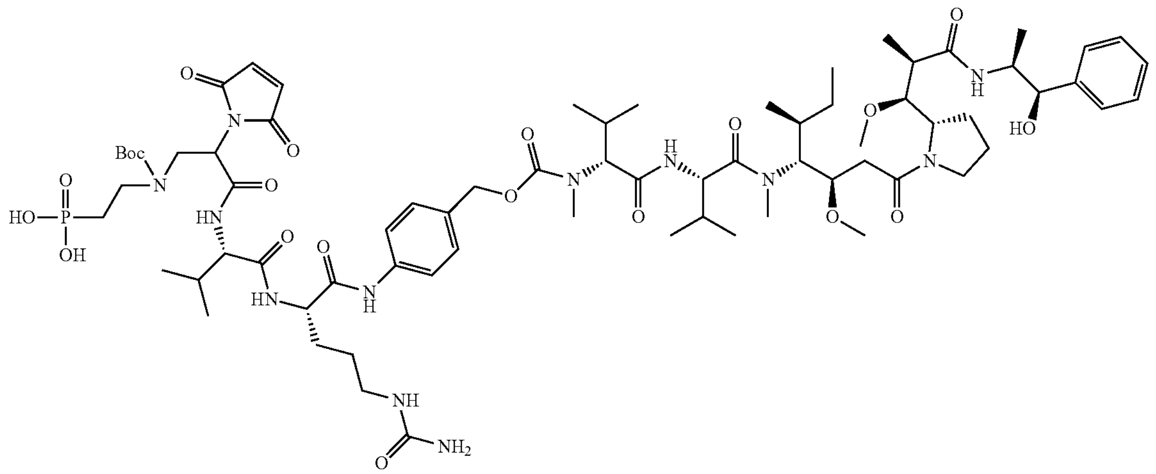

Compound 37 (260 mg, 0.17 mmol) was dissolved in a 25 ml round-bottom flask using 5 ml of distilled dichloromethane, after which bromotrimethylsilane (78 mg, 0.51 mmol) was added in an ice bath under nitrogen gas; the reaction was allowed to proceed overnight at room temperature under stirring and 1 ml of methanol was added the next morning, after which the reaction was allowed to proceed under stirring at room temperature for one hour and liquid phase analysis was used to confirm that Compound 37 had completely reacted. Post-Processing: The reaction solution was concentrated under reduced pressure, and the resulting residue was purified via HPLC. (Column: YMC-C18, 30 mm×450 mm, 10 μm, acetonitrile/water (0.2% TFA), flow rate 25 mL/min, detection at λ=214 nm)

Solvent A: 0.2% TFA water

Solvent B: Acetonitrile

Gradient: 0 min, 5% B, 0 to 10 min, 5 to 15% B, 10 to 20 min, 15 to 30% B, 20 to 35 min, 30 to 55% B, 35 to 45 min, 55 to 70% B, 45 to 55 min, 70% B, 55 to 60 min, 70 to 98% B.

The fraction with a retention time of 20 to 23 min was collected and lyophilized to obtain 140 mg of a white powdery solid, with a yield of 55%.

Example 39

Preparation of Compound 39

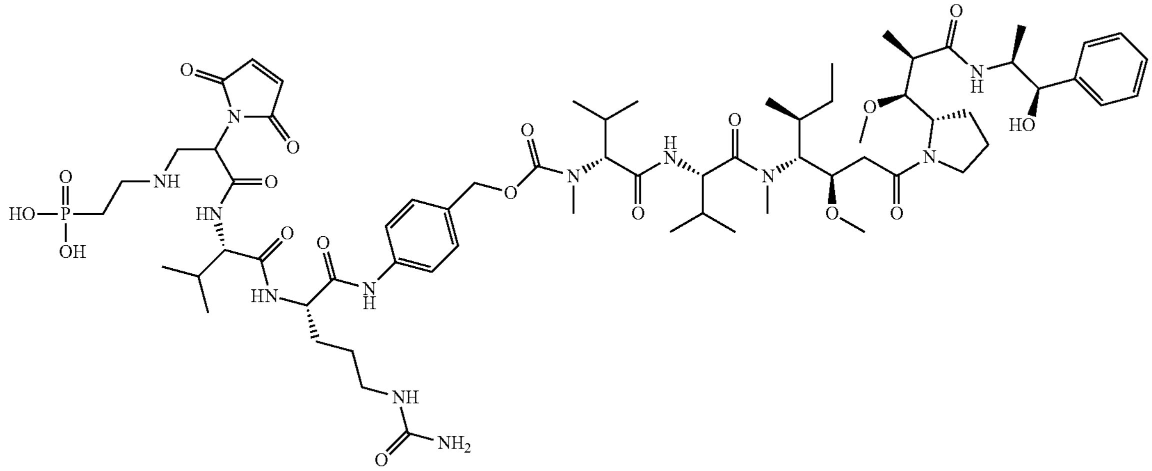

In a 25 ml round-bottom flask, 2 ml of dichloromethane was used to dissolve Compound 38 (120 mg, 0.08 mmol) under stirring, after which 800 microliters of trifluoroacetic acid was added dropwise in an ice bath; following dropwise addition, the reaction solution was moved to room temperature conditions and the reaction was allowed to proceed under stirring for one hour until the reaction was complete. Post-Processing: The reaction solution was concentrated under reduced pressure, and the resulting residue was purified via HPLC. (Column: YMC-C18, 30 mm×450 mm, 10 μm, acetonitrile/water (0.2% TFA), flow rate 25 mL/min, detection at λ=214 nm)

Solvent A: 0.2% TFA water

Solvent B: Acetonitrile

Gradient: 0 min, 5% B, 0 to 10 min, 5 to 15% B, 10 to 20 min, 15 to 30% B, 20 to 35 min, 30 to 55% B, 35 to 45 min, 55 to 70% B, 45 to 55 min, 70% B, 55 to 60 min, 70 to 98% B.

The fraction with a retention time of 18 to 19.5 min was collected and lyophilized to obtain 55 mg of a white powdery solid, with a yield of 49%. LC-MS m/z ($ES^+$): 1397.8 $(M+H)^+$ Example 40

Preparation of Compound 40

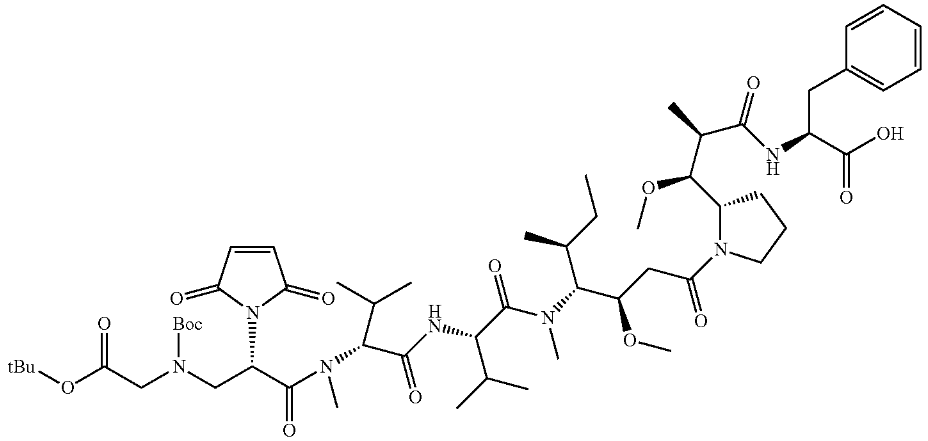 [SMILES: CC[C@H](C)[C@H]([C@@H](CC(=O)N1CCC[C@H]1[C@@H](OC)[C@@H](C)C(=O)N[C@@H](Cc1ccccc1)C(=O)O)OC)N(C)C(=O)[C@@H](NC(=O)[C@@H](C(C)C)N(C)C(=O)[C@H](CN(CC(=O)OC(C)(C)C)C(=O)OC(C)(C)C)N1C(=O)C=CC1=O)C(C)C]

Compound 7 (332 mg, 0.836 mmol) was dissolved in dry dichloromethane, pentafluorophenol (184 mg, 1 mmol) and dicyclohexylcarbodiimide (2 mmol) were added, and stirring was performed at room temperature for three hours until Compound 7 was eliminated. MMAF (460 mg, 0.585 mmol) and diisopropylethylamine (DIEA, 0.27 mL, 1.67 mmol) were added and dissolved in 15 mL of dry dichloromethane solution and the resulting reaction was allowed to proceed at room temperature for four hours under nitrogen gas. The solution was concentrated under reduced pressure, and the resulting residue was subject to separation using silica gel column chromatography (eluent: dichloromethane:methanol=50:1) to obtain 290 mg of product. LC-MS m/z ($ES^+$): 1168.8 $(M+H)^+$ Example 41

Preparation of Compound 41

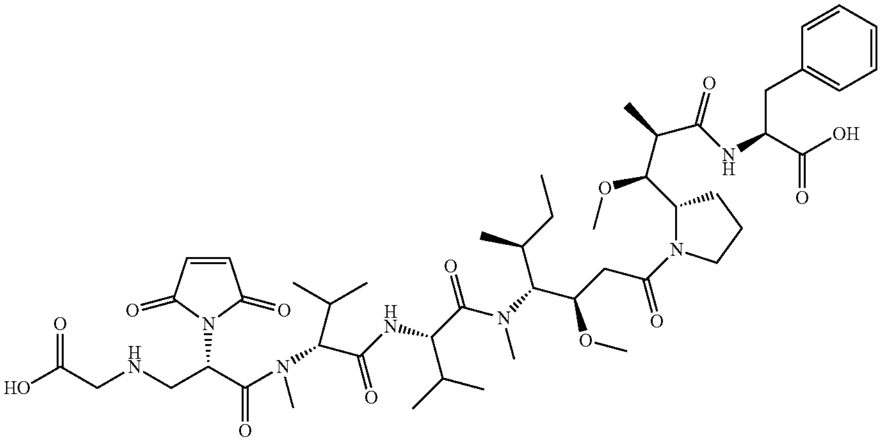 [SMILES: CC[C@H](C)[C@H]([C@@H](CC(=O)N1CCC[C@H]1[C@@H](OC)[C@@H](C)C(=O)N[C@@H](Cc1ccccc1)C(=O)O)OC)N(C)C(=O)[C@@H](NC(=O)[C@@H](C(C)C)N(C)C(=O)[C@H](CNCC(=O)O)N1C(=O)C=CC1=O)C(C)C]

100 mg of Compound 39 was dissolved in 10 mL of dry dichloromethane, 4 mL of trifluoroacetic acid was added, and the reaction was allowed to proceed at room temperature for two hours, followed by purification via HPLC.

(Column: YMC-C18, 30 mm×450 mm, 10 μm, acetonitrile/water (0.2% TFA), flow rate 25 mL/min, detection at 2=215 nm)

Solvent A: 0.2% TFA water

Solvent B: Acetonitrile

Gradient: 0 to 10 min, 95% A, 10 to 25 min, 95 to 70% A, 25 to 55 min, 70 to 40% A The fraction with a retention time of 33 min was collected and lyophilized to obtain 50 mg of product. LC-MS m/z ($ES^+$): 956.6 $(M+H)^+$ Example 42

Preparation of Compound 42

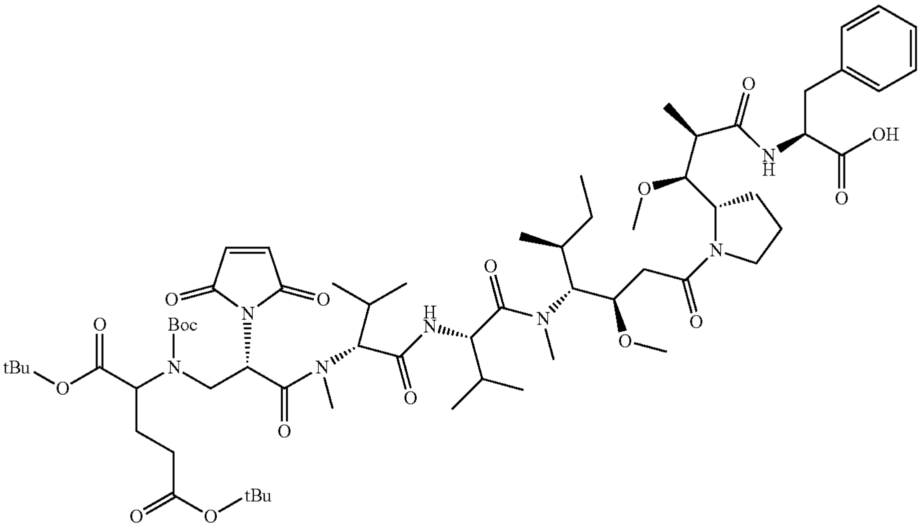 [SMILES: CC[C@H](C)[C@H]([C@@H](CC(=O)N1CCC[C@H]1[C@@H](OC)[C@@H](C)C(=O)N[C@@H](Cc1ccccc1)C(=O)O)OC)N(C)C(=O)[C@@H](NC(=O)[C@@H](C(C)C)N(C)C(=O)[C@H](CN(C(=O)OC(C)(C)C)C(CCC(=O)OC(C)(C)C)C(=O)OC(C)(C)C)N1C(=O)C=CC1=O)C(C)C]

Compound 16 (400 mg, 0.76 mmol) was dissolved in dry dichloromethane, pentafluorophenol (184 mg, 1 mmol) and dicyclohexylcarbodiimide (2 mmol) were added, and stirring was performed at room temperature for four hours until Compound 16 was eliminated. MMAF (389 mg, 0.49 mmol) and diisopropylethylamine (DIEA, 0.25 mL, 1.52 mmol) were added and dissolved in 15 mL of dry dichloromethane and the resulting reaction was allowed to proceed at room temperature for four hours under nitrogen gas. The solution was concentrated under reduced pressure, and the resulting residue was subject to separation using silica gel column chromatography (eluent: dichloromethane:methanol=50:1) to obtain 330 mg of product. LC-MS m/z ($ES^+$): 1296.8 $(M+H)^+$ Example 43

Preparation of Compound 43

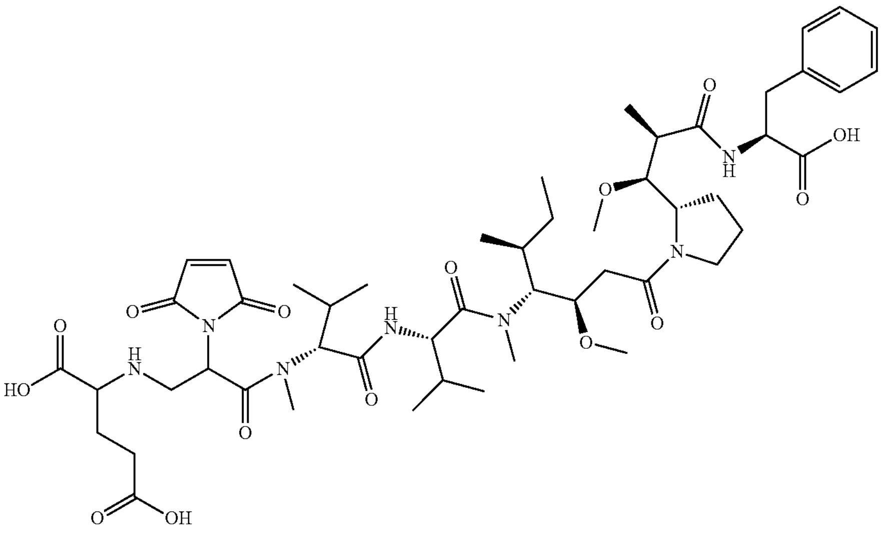 [SMILES: CC[C@H](C)[C@H]([C@@H](CC(=O)N1CCC[C@H]1[C@@H](OC)[C@@H](C)C(=O)N[C@@H](Cc1ccccc1)C(=O)O)OC)N(C)C(=O)[C@@H](NC(=O)[C@@H](C(C)C)N(C)C(=O)C(CNC(CCC(=O)O)C(=O)O)N1C(=O)C=CC1=O)C(C)C]

100 mg of Compound 41 was dissolved in 10 mL of dry dichloromethane, 4 mL of trifluoroacetic acid was added, and the reaction was allowed to proceed at room temperature for two hours, followed by purification via HPLC.

(Column: YMC-C18, 30 mm×450 mm, 10 μm, acetonitrile/water (0.2% TFA), flow rate 25 mL/min, detection at λ=215 nm)

Solvent A: 0.2% TFA water

Solvent B: Acetonitrile

Gradient: 0 to 10 min, 95% A, 10 to 25 min, 95 to 70% A, 25 to 55 min, 70 to 40% A The fraction with a retention time of 30 min was collected and lyophilized to obtain 48 mg of product. LC-MS m/z ($ES^+$): 1028.5 $(M+H)^+$ Example 44

The antibody-drug conjugate H-11 was prepared according to General Method B and reverse phase HPLC showed that the average drug/antibody ratio (DAR) value was 7.2.

Example 45

The antibody-drug conjugate H-20 was prepared according to General Method B and reverse phase HPLC showed that the average drug/antibody ratio (DAR) value was 7.2.

Example 46

The antibody-drug conjugate H-29 was prepared according to General Method B and reverse phase HPLC showed that the average drug/antibody ratio (DAR) value was 6.8.

Example 47

The antibody-drug conjugate H-39 was prepared according to General Method B and reverse phase HPLC showed that the average drug/antibody ratio (DAR) value was 7.0.

Example 48

The antibody-drug conjugate H-41 was prepared according to General Method B and reverse phase HPLC showed that the average drug/antibody ratio (DAR) value was 7.5.

Example 49

The antibody-drug conjugate H-43 was prepared according to General Method B and reverse phase HPLC showed that the average drug/antibody ratio (DAR) value was 7.7.

Example 50

Synthesis was continued to obtain the following drug-junction linkers:

General Formula I

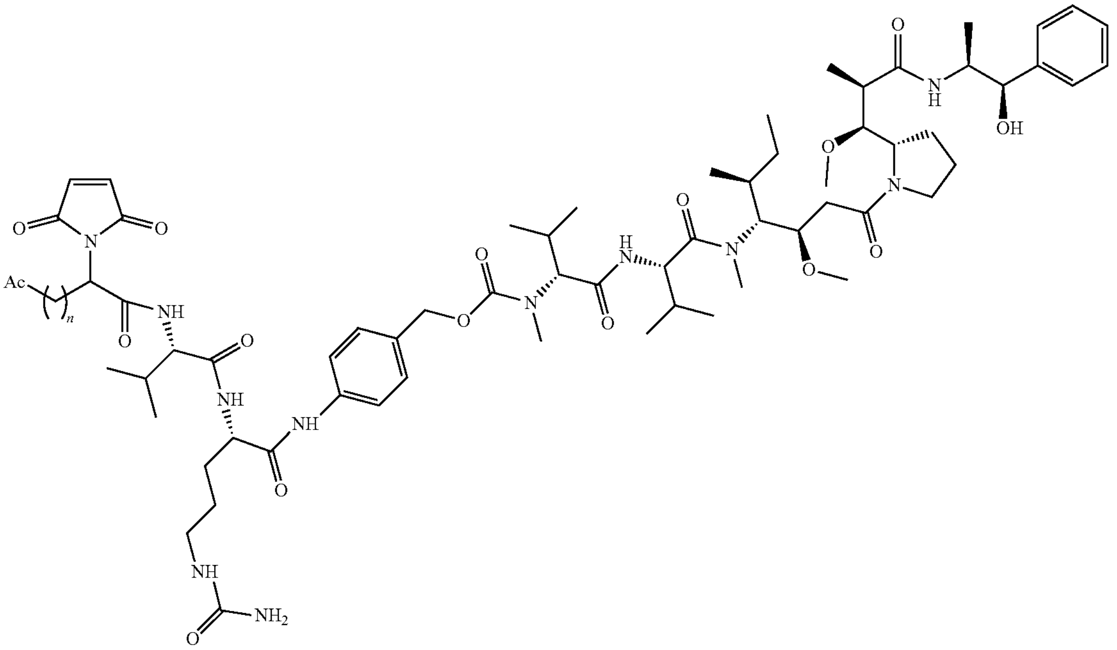

General Formula II

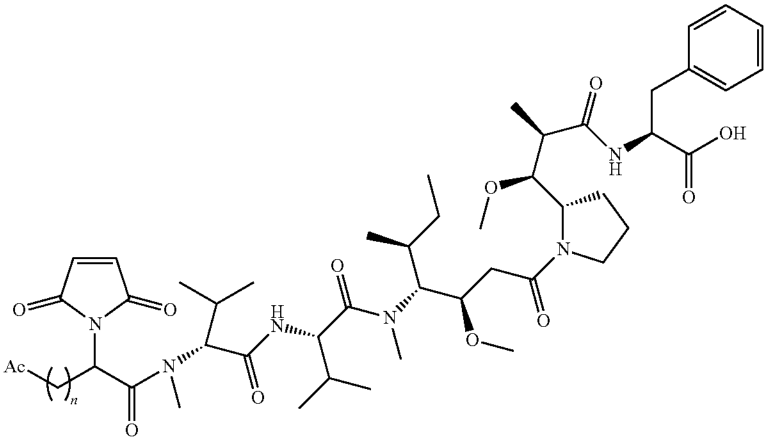

Where Ac represents a non-basic amino acid or oligopeptide, and the amino group in the amino acid is connected to an alkyl group;

n=1, 2, 3 . . . ;

Table 1 below summarizes the synthesis and characteristics of drug junctions containing different amino acids and oligopeptides. In the table, the first column from the left shows the compound number, the second column shows the class of amino acid, the third column shows the value of n, the fourth column shows the general method of synthesis and the fifth and sixth columns show the calculated mass of the drug junction and the mass as determined via mass spectrometry.

TABLE 1

| | Junction | | | | |
|---|---|---|---|---|---|
| Compound Number | Amino Acid Ac | n Value | Synthesis Method | Theoretical Molecular Weight | Actual Molecular Weight |
| 42 | Gly | 2 | General Formula I | 1360.7 | 1360.3 |
| 43 | Ala | 1 | General Formula II | 969.5 | 969.2 |
| 44 | Phe | 1 | General Formula II | 1045.6 | 1045.8 |
| 45 | Trp | 1 | General Formula I | 1452.7 | 1452.8 |
| 46 | Asp | 2 | General Formula I | 1418.7 | 1418.5 |

TABLE 1-continued

| Compound Number | Junction: Amino Acid Ac | Junction: n Value | Synthesis Method | Theoretical Molecular Weight | Actual Molecular Weight |
|---|---|---|---|---|---|
| 47 | Ser | 2 | General Formula II | 999.5 | 999.4 |
| 48 | Val | 1 | General Formula II | 997.5 | 999.6 |
| 49 | Pyrazole | 2 | General Formula I | 1470.7 | 1470.5 |
| 50 | Fur | 1 | General Formula II | 1023.5 | 1023.3 |
| 51 | Gly-Ala | 1 | General Formula I | 1431.4 | 1431.4 |

Abbreviations:
Gly: L-glycine,
Ala: L-alanine,
Phe: L-phenylalanine,
Trp: L-tyrosine,
Asp: L-aspartic acid,
Ser: L-serine,
Val: L-Valine Pyrazole: 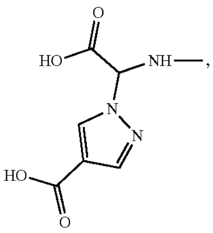

TABLE 1-continued

| Compound Number | Junction: Amino Acid Ac | Junction: n Value | Synthesis Method | Theoretical Molecular Weight | Actual Molecular Weight |
|---|---|---|---|---|---|

Fur: 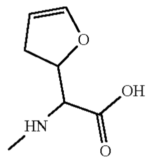

Examples 52 Through 56

To evaluate the stability, hydrophilicity, and pharmacological activity of ADCs prepared using an acidic self-stabilization junction, we prepared drug-junction linkages with acidic stabilizing joints according to the examples. These linkages all had an acidic stabilization junction, which was connected to the cytotoxic drug MMAE or MMAF via a cleavable or non-cleavable linker. As a comparison, a typical non-self-stabilization drug-junction linkage (hereinafter referred to as MC-VC-PAB-MMAE) was obtained according to methods given in the literature and a drug-junction linkage having a basic self-stabilization junction as described in the current patent (herein referred to as DPR-VC-PAB-MMAE) was obtained.

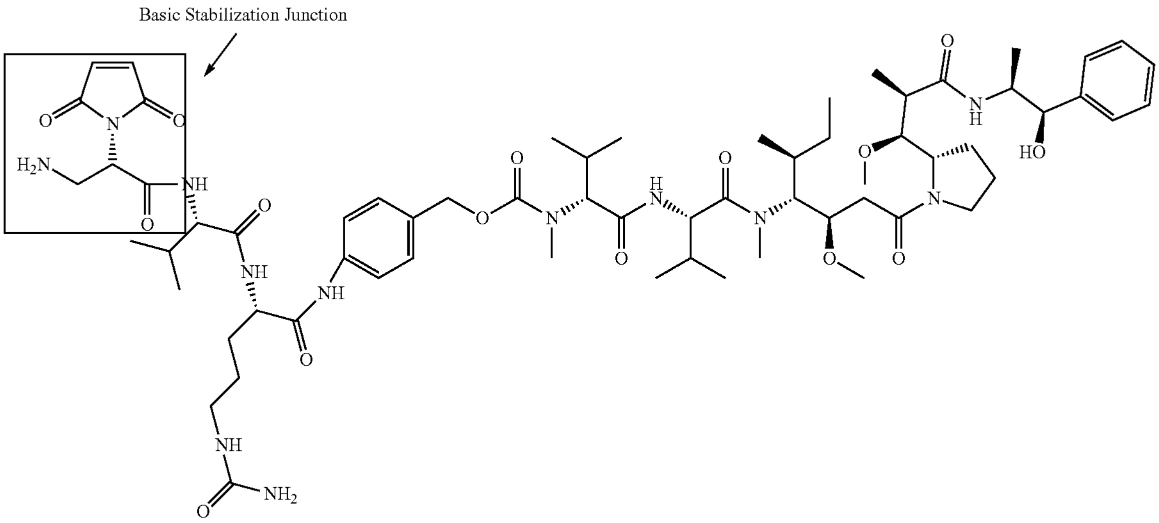

DPR-VC-PAB-MMAE

-continued

Typical MC Junction

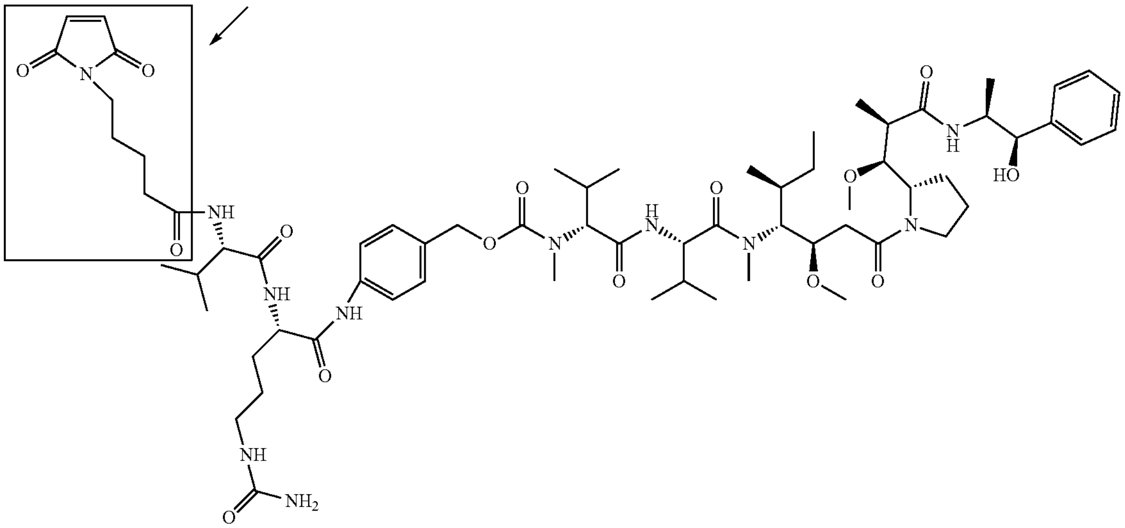

MC-VC-PAB-MMAE

Example 52: Plasma Stability In Vitro

The results of plasma stability studies conducted according to the method described in General Procedure D were as shown in the table below: ADCs with acidic stabilization junctions lost almost no drug during plasma incubation, whereas the typical MC junction ADC showed a very significant reduction in DAR after 72 hours of incubation. The experimental results demonstrate that an acidic stabilization junction can significantly improve the plasma stability of ADCs.

| Target Conjugate | 0 h DAR | 72 h DAR |
|---|---|---|
| H-11 | 7.2 | 6.8 |
| H-20 | 7.2 | 7.1 |
| H-29 | 6.8 | 6.4 |
| H-39 | 7.0 | 6.8 |
| H-41 | 7.5 | 6.9 |
| H-43 | 7.7 | 6.4 |
| MC-VC-PAB-MMAE | 7.2 | 2.3 |

Example 53: SEC-HPLC Detection

ADC samples obtained via conjugation were centrifuged at 14,000 rpm for five minutes and the supernatant was taken for analysis.

Instrument: Waters e2695 (2489UV/Vis)

Chromatography column: TSKgel G3000SWXL (7.8×300 mm, 5 μm)

Mobile phase: A: 50 mM PB, 300 mM NaCl, 200 mM Arg, 5% IPA, pH 6.5

Mobile Phase A was eluted isocratically for 30 minutes; flow rate: 0.714 ml/min, column temperature: 25° C., detection wavelength: 280 nm.

The degree of aggregation of each ADC was obtained via SEC-HPLC and SEC-HPLC peak plots are shown in FIGS. 2A through 2H; the corresponding data are summarized in the following table, where the monomer rate was significantly increased and the degree of aggregation was significantly reduced in ADCs which incorporated an acidic stabilization junction.

| Target Conjugate | Monomer Ratio | Aggregation Rate |
|---|---|---|
| H-11 | 96.25% | 3.75% |
| H-20 | 98.85% | 1.15% |
| H-29 | 98.26% | 1.74% |
| H-39 | 98.86% | 1.14% |
| H-41 | 97.02% | 2.98% |
| H-43 | 96.54% | 3.46% |
| MC-VC-PAB-MMAE | 67.51% | 32.46% |
| DPR-VC-PAB-MMAE | 79.10% | 20.90% |

Example 54

Murine In Vivo PK Experiments

Figure 3:
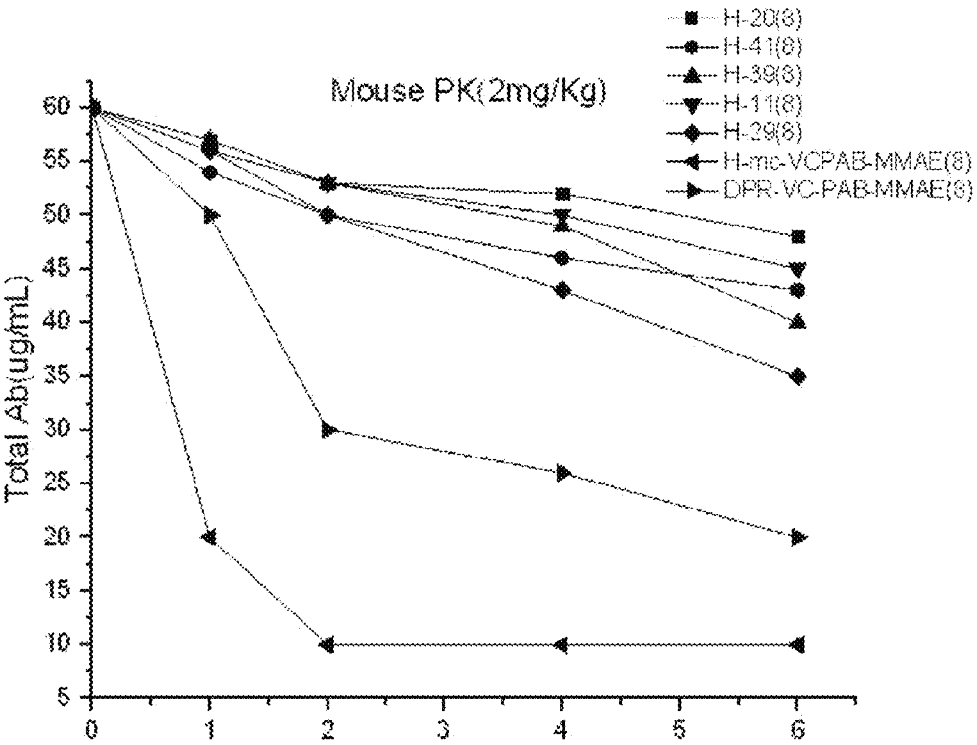
FIG. 3 shows the results of in vivo stability studies of unconjugated antibodies, ADCs with acidic stabilization junctions and control ADCs.

The PK properties of ADCs (with a load of 8) were determined using a murine model. Drug was administered via a single intravenous injection in the tail at a dose of 2 mg/kg, and the total antibody (Total Ab) concentration in the blood was assayed according to General Procedure B; the results are shown in FIG. 3. The results of the experiment show that, in a murine model, acidic stabilization junction ADCs showed significantly improved PK properties with total antibodies maintained at a higher concentration for a longer period of time.

Example 55

Hydrophobic Interaction Chromatography (HIC) Assay

Figure 4:
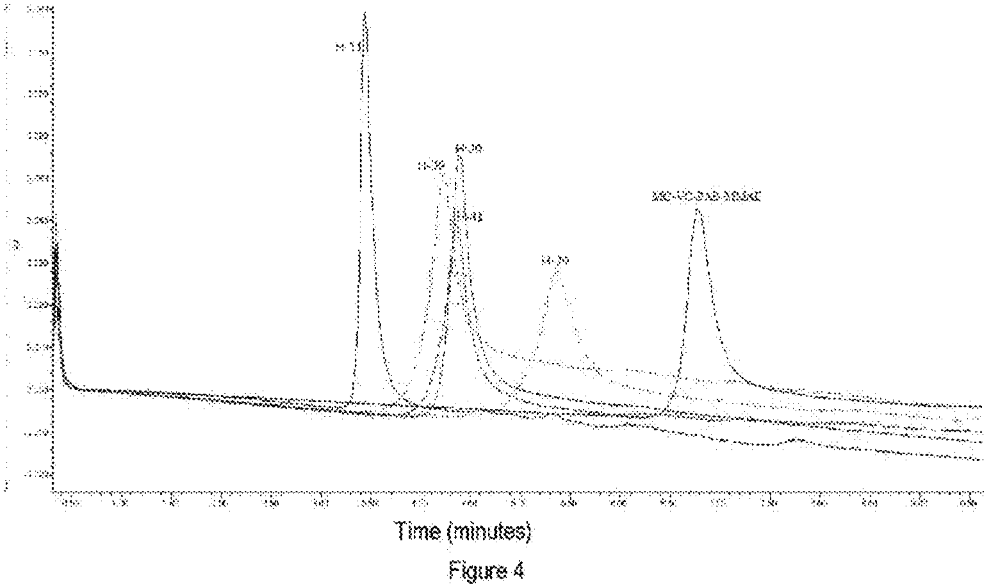
FIG. 4 shows HIC chromatograph results for ADCs with acidic stabilization junctions and a control ADC.

Following complete reduction of IgG1 antibody to 8 thiols per antibody according to General Procedure A, corresponding antibody-drug conjugates were prepared via non-specific coupling. ADCs with acidic stabilization junctions and conventional junctions ADC (i.e., MC-VC-PAB-MMAE) with eight drug units per antibody were further separated and purified via hydrophobic interaction chromatography and hydrophobic interaction chromatography (HIC) was used to perform an ADC analysis according to General Procedure C. ADCs with greater hydrophobicity, or larger drug/molecule ratios eluted at later retention times. The results are shown in FIG. 4: ADCs with acidic junctions showed relatively short retention times in HIC, with the MC-VC-PAB-MMAE antibody conjugate exhibiting the longest retention time. The experimental results demonstrate that ADC molecules having an acidic stabilization junction exhibit better hydrophilicity.

Example 56

In Vivo Drug Efficacy Experiments (Cell Proliferation Assay)

Figure 5:
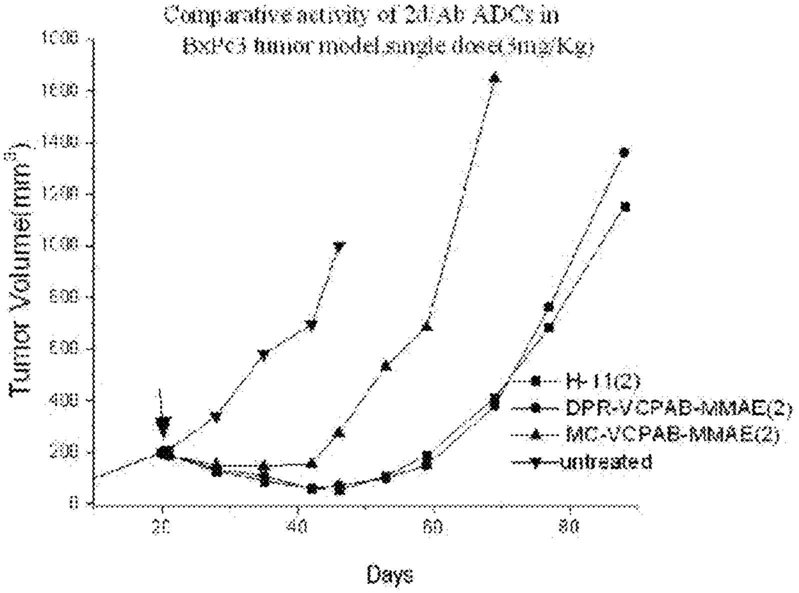
FIG. 5 shows in vivo efficacy results for ADCs with acidic stabilization junctions and a control ADC.
Figure 6:
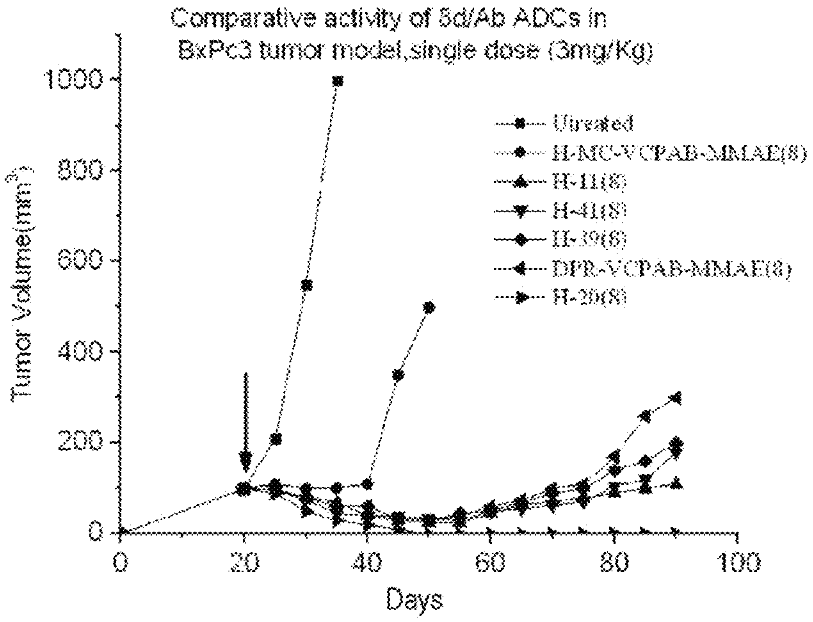
FIG. 6 corresponds to a graph showing the experimental results obtained for Example 56.

Human pancreatic adenocarcinoma cells (BxPc3) were cultured in vitro and inoculated subcutaneously into backs of BALB/c nude mice at an inoculation cell count of $5\times10^6$ and after the tumors had grown to 100 to 200 $mm^3$, the animals were grouped and given a single dose of ADC at 3 mg/kg (injected via the tail vein) while a vehicle-control group was also established; mice were subject to regular weighing and measurements of tumor volume and drug efficacy with respect to the BxPc3 model was evaluated by examining the tumor suppression efficacy of the ADCs as well as other indicators. The experimental results are shown in FIGS. 5 and 6. The results show that ADCs having an acidic stabilization junction exhibit similar efficacy to Dpr-MC-VC-PAB-MMAE at DAR=2, and are significantly superior to Mc-VC-PAB-MMAE in this respect. At a high drug load of DAR=8, the same ADCs showed good efficacy in a BxPc3 murine subcutaneous transplantation tumor model.

The invention claimed is:

1. An antibody-drug conjugate or its pharmaceutically acceptable salt thereof as shown in Formula I:

I

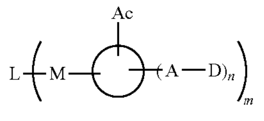

wherein:

the circle represents a scaffold, wherein the scaffold comprises a $C_{1-8}$ alkylidene group, a $C_{1-8}$ heteroalkylidene group, a $C_{6-10}$ arylidene group, or a $C_{4-10}$ heteroarylidene group;

L comprises an antibody, an antibody fragment or a protein;

M comprises a succinimide group;

Ac is connected to the scaffold through an amino group, wherein Ac comprises an acidic unit that serves to stabilize the antibody-drug conjugate, and wherein Ac comprises a fragment consisting of at least one amino group and at least one acidic group or an oligopeptide group consisting of a plurality of amino acid units;

D comprises a drug unit;

A comprises a linker;

m is an integer selected from 1 to 20; and n is 1 or 2.

2. The antibody-drug conjugate or its pharmaceutically acceptable salt thereof as described in claim 1, wherein M comprises a succinimide group, and wherein said antibody corresponds to an antibody for a cell surface receptor and tumor-associated antigen.

3. The antibody-drug conjugate or its pharmaceutically acceptable salt thereof as described in claim 1, wherein the acidic unit of Ac is selected from a group consisting of carboxylic acid, phosphoric acid, phosphite, and sulfonic acid groups, and wherein the drug unit D is selected from a group consisting of auristatins, amantins, camptothecins, maytansinoids, analogs of dolastatin 10, cachymycins, calicheamicins, doxorubicins, duocarmycins, rachelmycin (CC-1065), goitrogens, icticam, irinotecan, ixitecan, their pharmaceutically acceptable salts or derivatives thereof.

4. The antibody-drug conjugate or its pharmaceutically acceptable salt thereof as described in claim 1, wherein Ac comprises an acidic amino acid group or an acidic oligopeptide group, and wherein the drug unit D comprises autistatins, amantins, camptothecins, or their pharmaceutically acceptable salts or derivatives thereof.

5. The antibody-drug conjugate or its pharmaceutically acceptable salt thereof as described in claim 1, wherein the heteroalkylidene group comprises one or more heteroatoms selected from a group consisting of O, S, N or P atoms; wherein the arylidene group is selected from a group consisting of phenyl, naphthyl or diphenyl; wherein the heteroarylidene group is selected from a group consisting of pyridyl, pyridazinyl, pyrazinyl, pyrimidinyl, indolyl, quinolinyl, isoquinolinyl, isothiazolyl, pyrazolyl, indazolyl, pteridyl, imidazolyl, triazolyl, tetrazolyl, oxazolyl, isoxazolyl, thiadiazolyl, pyrrole, thiazolyl, furanyl and thiophene.

6. The antibody-drug conjugate or its pharmaceutically acceptable salt thereof as described in claim 1, wherein A comprises a cleavable linker or a non-cleavable linker.

7. The antibody-drug conjugate or its pharmaceutically acceptable salt thereof as described in claim 1, wherein said drug unit D comprises a cytotoxic drug, a drug for treating autoimmune disease, or an anti-inflammatory drug.

8. The antibody-drug conjugate or its pharmaceutically acceptable salt thereof as described in claim 7, wherein the drug unit D is selected from a group consisting of maitansine drugs, australin drugs, benzodipyrrole drugs, pyrrolozodiazole drugs, amantin and camptothecine compounds, their pharmaceutically acceptable salts or derivatives thereof.

9. The antibody-drug conjugate or its pharmaceutically acceptable salt thereof as described in claim 6, wherein A has a structure as shown in the following formula:

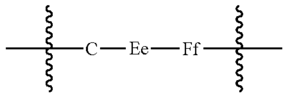

wherein C represents an extensible unit at the end, E represents a cleavable unit, F represents a spacer unit, subscripts e and f each is independently 0 or 1, the wavy line on the left represents a connection site to the scaffold and the wavy line on the right represents a connection site to the drug unit.

10. The antibody-drug conjugate or its pharmaceutically acceptable salt thereof as described in claim 9, wherein E is configured to be cleaved off from the drug unit D or the spacer unit F by a tumor-associated protease or under an acidic pH.

11. The antibody-drug conjugate or its pharmaceutically acceptable salt thereof as described in claim 9, wherein F is selected from a group consisting of p-aminobenzyl alcohol, ethylenediamine units, and their derivatives thereof.

12. The antibody-drug conjugate or its pharmaceutically acceptable salt thereof as described in claim 5, wherein the scaffold comprises $C_{1-8}$ alkylidene or $C_{1-8}$ heteroalkylidene.

13. The antibody-drug conjugate or its pharmaceutically acceptable salt thereof as described in claim 12, wherein the scaffold comprises a $C_{1-3}$ alkylidene.

14. The antibody-drug conjugate or its pharmaceutically acceptable salt thereof as described in claim 1, wherein Ac is (D/L) glycine.

15. A method of making a pharmaceutical composition for treating cancer, immune disease or inflammation using the antibody-drug conjugate or its pharmaceutically acceptable salt thereof as described in claim 1, comprising combining the antibody-drug conjugate or its pharmaceutically acceptable salt thereof as described in claim 1 with a pharmaceutically acceptable carrier.

16. A pharmaceutical composition, comprising the antibody-drug conjugate or its pharmaceutically acceptable salt thereof as described in claim 1 and a pharmaceutically acceptable carrier.

17. A method of treating cancer, immune disease or inflammation in a subject in need thereof, comprising administering to the subject an effective amount of the antibody-drug conjugate of claim 1, or a pharmaceutically acceptable salt thereof, or the pharmaceutical composition of claim 16.

18. The antibody-drug conjugate or its pharmaceutically acceptable salt thereof as described in claim 1, wherein

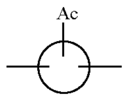

is

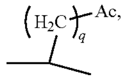

wherein q is an integer ranging from 1 to 8, and wherein the drug unit D comprises auristatins, amantins, camptothecins, or its pharmaceutically acceptable salts or derivatives thereof.

* * * * *